(12) United States Patent
Takagi et al.

(10) Patent No.: US 8,298,484 B2
(45) Date of Patent: Oct. 30, 2012

(54) ANALYZING APPARATUS

(75) Inventors: Yasumitsu Takagi, Kyoto (JP); Hisakazu Sugie, Kyoto (JP); Toshiyuki Otsuki, Kyoto (JP); Norimasa Nishida, Kyoto (JP); Yoshikiyo Hongo, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 781 days.

(21) Appl. No.: 11/579,990

(22) PCT Filed: May 10, 2005

(86) PCT No.: PCT/JP2005/008504
§ 371 (c)(1),
(2), (4) Date: May 22, 2007

(87) PCT Pub. No.: WO2005/109008
PCT Pub. Date: Nov. 17, 2005

(65) Prior Publication Data
US 2007/0264157 A1    Nov. 15, 2007

(30) Foreign Application Priority Data

May 10, 2004  (JP) ................ 2004-140353
May 10, 2004  (JP) ................ 2004-140354
May 10, 2004  (JP) ................ 2004-140355

(51) Int. Cl.
*G01N 15/06* (2006.01)
(52) U.S. Cl. ............ 422/65; 422/68.1; 422/62; 422/64; 422/63; 422/82.02; 436/134
(58) Field of Classification Search ............ 422/60–69, 422/82.01–82.09; 436/164
See application file for complete search history.

(56) References Cited

U.S. PATENT DOCUMENTS

| 5,281,395 | A | 1/1994 | Markart et al. |
| 2001/0022348 | A1* | 9/2001 | Furusato et al. ............ 250/576 |
| 2002/0132363 | A1 | 9/2002 | Rehm |
| 2003/0169426 | A1 | 9/2003 | Peterson et al. |
| 2003/0185710 | A1 | 10/2003 | Matsuda et al. |

FOREIGN PATENT DOCUMENTS

EP    0997715 A2    5/2000
(Continued)

OTHER PUBLICATIONS

International Search Report for the corresponding PCT application: PCT/JP2005/008504, mailed Aug. 23, 2005.

*Primary Examiner* — In Suk Bullock
*Assistant Examiner* — Sharon Pregler
(74) *Attorney, Agent, or Firm* — Fox Rothschild LLP

(57) ABSTRACT

The present invention relates to an analyzer (1) which includes a placement part (11) for placing an analysis piece, and a photometric measurer (7) for photometric measurement of the analysis piece (2). In the analyzer (1), the placement part (11) holds the analysis piece (2) in such a way that a row of reagent pad (20) on the analysis piece (1) lie in right-and-left directions (D3, D4). The photometric measurer (7) is farther from a front than the placement part (11). The analysis piece (2) placed on the placement part (11) is conveyed from front toward rear (Direction D1), with the row of reagent pads (20) laid in right-and-left directions (D3, D4), toward the photometric measurer (7).

35 Claims, 17 Drawing Sheets

FOREIGN PATENT DOCUMENTS

| | | |
|---|---|---|
| JP | 4-109169 | 4/1992 |
| JP | 11-38013 | 2/1999 |
| JP | 2000-55922 | 2/2000 |
| JP | 2002-303625 | 10/2002 |
| WO | 02/08753 A2 | 1/2002 |
| WO | WO 02/16043 | 2/2002 |
| WO | 03/044500 A1 | 5/2003 |

* cited by examiner

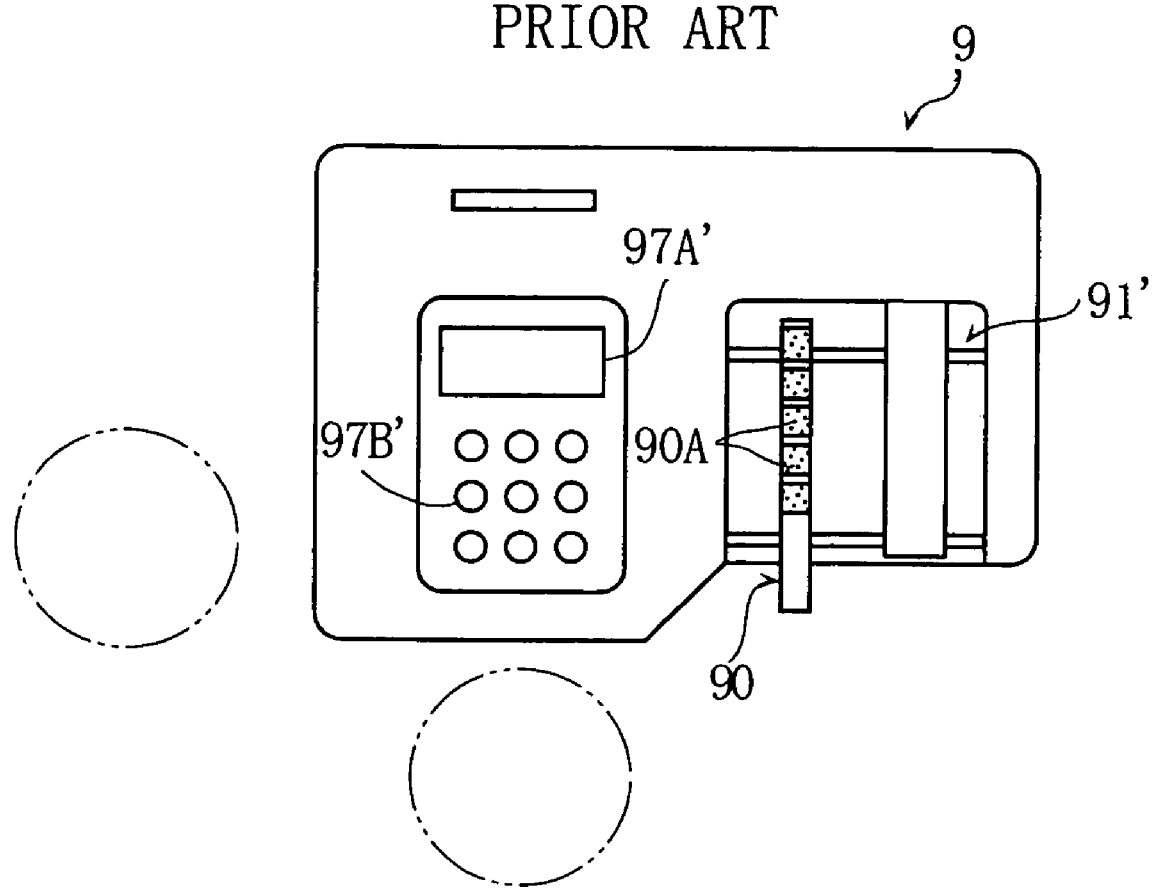

ANALYZING APPARATUS

TECHNICAL FIELD

The present invention relates to analyzers which make use of an analysis piece for analyzing a specific component in a sample such as urine.

BACKGROUND ART

FIG. 18 and FIG. 19 show an analyzer which uses a test piece and performs semi-automatic analysis for various components in urine (See Patent Document 1 for example). In the illustrated analyzer 9, a test piece 90 which includes a plurality of reagent pads 90A is wetted with urine and is placed by the user onto a placement part 91 of the analyzer 9, whereupon photometric urine analysis is performed automatically. More specifically, the test piece 90 which is placed on the placement part 91 is first moved by a carrier arm 92 to a photometric region 93. In the photometric region 93, the test piece undergoes optical measurement by a photometric measurer 94. After the measurement, the test piece 90 is moved by the carrier arm 92 into a disposal box 95.

In the analyzer 9, the placement part 91 is on the left-hand side (on the side N1). This provides the following advantages. If the user is right-handed, he will normally use his left hand to hold a urine container 96, or place the container 96 onto the left-hand side (on the side N1) or in front (on the side N3) of the analyzer 9 in order to wet the reagent pads 90A of the analyzer 9 with urine. For this reason, an arrangement as shown in FIG. 20, where a placement part 91' is on the right-hand side, would make it necessary that the test piece 90 wetted with urine must be moved over a display panel 97A' and an operation panel 97B' of the analyzer 9' before being placed onto the placement part 91'. As a result, the analyzer 9' has a risk that the urine will drip from the test piece 90, spattering onto the display panel 97A' or the operation panel 97B', which will pose hygienic concerns. Meanwhile in the analyzer 9', in order to protect the display panel 97A' and the operation panel 97B' from being stained with urine, the user must make utmost care when placing the test piece 90 onto the placement part 91', so this arrangement is inconvenient. On the contrary, the analyzer 9 in FIG. 18 and FIG. 19 has an arrangement so that the placement part 91 comes on the left-hand side (on the side N1) of the user. Thus, the arrangement offers such an advantage that it is easy to place the test piece 90 onto the placement part 91, and to keep a high level of hygienic cleanliness.

Further, in the analyzer 9, a guide wall 98 is provided between the placement part 91 and the photometric region 93. The guide wall 98 is to correct the attitude of the test piece 90 while the test piece 90 is being moved from the placement part 91 to the photometric region 93, and is configured to have a tapered surface 99 which becomes closer to the front (in Direction N3) as it becomes farther away (in Direction N2) from the placement part 91. Thus, during the movement to the photometric region 93, the test piece 90 which is pushed by the carrier arm 92 moves while keeping contact with the guide wall 98 (tapered surface 99), and is made parallel to the carrier arm 92. As a result, the test piece 90 is put into a predetermined attitude (in which the reagent pads 90A line up in Directions N3, N4 by the time when the test piece 90 comes to an end 98A of the guide wall 98, i.e. the photometric region 93. Therefore, the analyzer 9 offers such an advantage that the test piece 90 can be moved to take a predetermined attitude with respect to the photometric region 93 even if the test piece 90 is placed not very carefully with respect to the placement part 91.

Further, in the analyzer 9, photometric measurement of the test piece 90 in the photometric measurer 94 is performed by casting a light to the test piece 90 and receiving a light reflected by the test piece 90 while moving the photometric measurer 94 in an reciprocating trip along the Directions N3, N4 for example. With this arrangement, the analyzer 9 can obtain information necessary for analyzing the test piece 90, from the test piece 90.

However, the analyzer 9 is designed primarily for right-handed users, with the placement part 91 disposed on the left-hand side. This poses the same disadvantage to the left-handed users, as the disadvantage to the right-handed users who have to use the analyzer 9' shown in FIG. 20.

Further, in the analyzer 9, it is necessary that after the reagent pads 90A on the test piece 90 are wetted with urine, the test piece 90 must be placed on the placement part 91 in such a way that the reagent pads 90A will line up in the fore-back directions (Directions N3, N4). Specifically, during the sequence of wetting with urine and placing the test piece 90, the tip of the test piece 90 must undergo a major pivoting movement. In order to move the test piece 90 in such a way, the user must make a major flip on his wrist, which means that moving the test piece 90 from the container 96 onto the placement part 91 is not necessarily an easy job. Further, when the tip of the test piece 90 which is wetted with urine is flipped to travel a long way, urine is very likely to spatter, which poses a hygienic concern or poses an excessive burden on the user to pay much caution.

Moreover, the arrangement that the attitude of the test piece 90 is corrected by the tapered surface 99 has a problem: If the tapered surface 99 is made steep (if curvature is decreased), the corner of the test piece 90 will be caught by the tapered surface 99 while the test piece 90 is being moved, making it impossible to maintain the parallelism of the test piece 90 to the carrier arm 92. On the other hand, in order to carry the test piece 90 while keeping the test piece 90 in parallel to the main carrier arm 92, the tapered surface 99 must have a small gradient (curvature must be large). In this case, the travel distance for the test piece 90 must be long, resulting in a long dimension of the analyzer 9 in Directions N1, N2, and making the analyzer inconveniently large.

Further, in the arrangement which makes the reciprocating travel of the photometric measurer 94 in the Directions N1, N2 for photometric measurement of a single test piece 90, at least a half of the travel distance of the photometric measurer 94 does not contribute to the photometric measurement of the test piece 90. This means that in the analyzer 9, the returning travel of the photometric measurer 94 to its original position contributes to nothing by itself, or the photometric measurer 94 is moved back to the original position wastefully. As a result, in the analyzer 9, there is a waste of time in the travel of the photometric measurer 94 in the photometric measurement cycle. This means that there is a long time-interval when a plurality of test pieces 90 are subjected to continuous photometric measurement, and if this inconvenience is to be solved, an expensive drive mechanism will have to be called for, leading to an increased cost of manufacture.

In addition, a longer travel distance of the photometric measurer 94 per photometric measurement means greater wear and tier, and shorter life of the traveling mechanism for the photometric measurer 94. If such a problem is to be solved, it is necessary to increase durability of the traveling mechanism for the photometric measurer 94, leading to an increased cost of manufacture.

Patent Document 1: JP-A-2000-55922

DISCLOSURE OF THE INVENTION

It is therefore an object of the present invention to provide an analyzer which is convenient for both left- and right-handed users, does not require the user to flip his/her wrist when placing the analysis piece, and reduces burden on the user in the analyzing operation.

Further, another object of the present invention is to enable that the analysis piece is brought to a target place at a desired attitude, without increasing the size of the analyzer.

Still another object of the present invention is to provide an analyzer capable of performing high-speed photometric measurement (analysis) operation, without increasing manufacturing cost while keeping a long service life.

An analyzer according to the present invention analyzes sample, using an analysis piece carrying one or a plurality of reagent pads on a base material. The analyzer includes a placement part for placement of the analysis piece, and a photometric measurer for photometric measurement of the analysis piece. The analysis piece is moved in a conveying direction from the placement part toward the photometric measurer. The placement part is arranged to allow the placement of the analysis piece in a state selected from two options: a state in which a first end of the base material provided with at least one reagent pad is oriented in a first direction perpendicular to the conveying direction with respect to a second end of the base material not provided with the reagent pad; and a state in which the first end is oriented in a second direction opposite to the first direction with respect to the second end.

In the analyzer according to the present invention, the reagent pads include a first and a second reagent pads for example. In this case, the placement part allows the placement of the analysis piece in a state selected from: a state in which the first reagent pad is oriented in the first direction with respect to the second reagent pad; and a state in which the first reagent pad is oriented in the second direction with respect to the second reagent pad.

In the analyzer according to the present invention, the analysis piece is conveyed from the placement part toward the photometric measurer, with the reagent pads lined in right-and-left directions for example.

The photometric measurer is farther from a front of the analyzer than the placement part for example. In this case, the analysis piece is conveyed from a side closer to the front toward a side farther from the front.

Preferably, the placement part is open to an upward direction as well as to the first and the second directions.

For example, the photometric measurer is capable of making a reciprocating travel between a first stand-by position provided on the side of the first direction and a second stand-by position provided on the side of the second direction, along a row of the reagent pads. In this case, preferably, the analyzer further includes: a controller for controlling an operation of the photometric measurer in such a way that the photometric measurer is moved from the first stand-by position to the second stand-by position and then made stand by at the second stand-by position if the photometric measurer is at the first stand-by position whereas the photometric measurer is moved from the second stand-by position to the first stand-by position and then made stand by at the first stand-by position if the photometric measurer is at the second stand-by position, for each analysis of the analysis piece. Further, a computing part which makes calculation necessary for analyzing the sample for each reagent pad, based on a result of photometric measurement at the photometric measurer during the travel of the photometric measurer from the first stand-by position to the second stand-by position or from the second stand-by position to the first stand-by position.

According to the present invention, the analysis piece may include a baseline part provided on an extension of the row of the reagent pads and closely to the row of the reagent pads. In this case, the computing part makes calculation necessary for analyzing the sample, using a method including: a first step of obtaining a time course of light reception amount during the trip of the photometric measurer from the first stand-by position to the second stand-by position or from the second stand-by position to the first stand-by position; a second step of detecting a baseline part data region representing the baseline part in the time course; and a third step of obtaining a reagent pad data region for each of the reagent pads, using the baseline part data region as a baseline. The computing part checks if the travel of the photometric measurer was from the first stand-by position to the second stand-by position or from the second stand-by position to the first stand-by position, and takes the travel direction of the photometric measurer into account when obtaining the reagent pad data regions in the third step. When the computing part is configured as the above, preferably, a dimension of each reagent pad along the row of the reagent pads on the analysis piece is greater than a dimension of the baseline part along the row.

The analyzer may be capable of conveying a plurality of the analysis pieces continuously to the photometric measurer, the photometric measurer making photometric measurement continuously to the analysis pieces.

The photometric measurer includes a plurality of light emitters and an optical receiver. In this case, the light emitters cast light diagonally to each reagent pad, and the optical receiver receives reflected light coming upward from each reagent pad. The light emitters are disposed in a point symmetry as viewed from above, with the optical receiver representing a center of the symmetry. Alternatively, the optical receiver is on a hypothetical straight line extending along the conveying direction, and the light emitters are disposed in a line symmetry as viewed from above, with respect to the hypothetical straight line.

The analyzer according to the present invention may further include correction means for correction of a positional variation of the analysis piece in the first and the second directions, from a time of placement of the analysis piece onto the placement part to a time of photometric measurement at the photometric measurer.

The correcting means selectively takes a state of restricting the analysis piece in the first and the second directions, or a state of not restricting the analysis piece. In this case, the correction means preferably includes one or more pivoting members pivoted to select the state of restricting the analysis piece in the first and the second directions or the state of not restricting the analysis piece.

The one or more pivoting members includes a first and a second pivoting members each having a holding portion for restricting the analysis piece, the holding portions being able to come closer to and go away from each other. In this case, the correction means restricts the analysis piece in the first and the second directions by pivoting the first and the second pivoting members in a way to bring the holding portions closer to each other, and ceases the restriction on the analysis piece in the first and the second directions by pivoting the first and the second pivoting members in a way to bring the holding portions away from each other.

The analyzer according to the present invention may further include a moving member capable of making a reciprocating movement in the conveying direction and in the direction opposite thereto, for sliding the analysis piece to or close to a position provided with the first and the second pivoting members. In this case, the first and the second pivoting members preferably pivot in association with the movement of the moving member.

The first and the second pivoting members may pivot to restrict the analysis piece in the first and the second directions when the moving member changes its state from a non-interfering state to an interfering state, and pivot not to restrict the analysis piece in the first and the second directions when the mover changes its state from the interfering state to the non-interfering state. More specifically, the first and the second pivoting members may have interference counter portions for interference by the moving member, and the holding portions pivot to restrict the analysis piece upon downward displacement of the interference counter portions. On the other hand, the moving member has an interferer for interference with the interference counter portions. In this case, preferably, at least one of the interference counter portions and the interferer has a tapered surface for applying a downward force to the interference counter portions upon interference of the interferer with the interference counter portions. The interference counter portions may protrude in a direction opposite to the conveying direction. The interferer may have the tapered surface and protrudes in the conveying direction.

The correction means preferably corrects position variation of the analysis piece in the first and the second directions while the analysis piece stops at a correction position provided between the placement part and the photometric measurer.

In the analyzer according to the present invention, the correction of position variation of the analysis piece in the first and the second directions may be performed on a side closer to a front of the analyzer than a place provided with correction means. More specifically, variation of the analysis piece in the conveying direction is corrected by sandwiching the analysis piece between the moving member and an upright wall extending in the first and the second directions.

The analyzer according to the present invention may further include excess sample removing means for removing excess sample from the analysis piece. In this case, the excess sample removing means removes excess sample from the analysis piece and may correct position variation of the analysis piece as well in the conveying direction, by sandwiching the analysis piece between itself and the moving member. The excess sample removing means may remove excess sample by means of capillary force upon contact with the analysis piece. In the analyzer according to the present invention, the analysis piece may be moved over the excess sample removing means to a position provided with the correction means after being contacted with the excess sample removing means.

The analyzer according to the present invention may further includes a disposal box for storing analysis pieces which have undergone photometric measurement at the photometric measurer, and a breaker mechanism for breaking a pile of analysis pieces in the disposal box.

The breaker mechanism may include a contact element for making contact with the pile of analysis pieces in the disposal box. Preferably, the breaker mechanism selectively takes a first state in which at least part of the contact element is in the disposal box to be contactable with the pile of analysis pieces and a second state in which the contact element is entirely out of the disposal box.

The analyzer according to the present invention may further include a conveying mechanism for conveying the analysis piece in the conveying direction for at least part of a conveying route of the analysis piece which starts from the placement part toward the photometric measurer. Specifically, the conveying mechanism includes a rotating mover which rotates for conveying the analysis piece. In this case, preferably, the contact element repeats a cycle of the first state and the second state in association with the movement of the rotating mover. Preferably, the contact element is rocked by the rotating mover, and is provided by a leaf spring.

BRIEF DESCRIPTION OF THE DRAWINGS

FIG. 20 is a plan view for describing advantages of the analyzer in FIG. 18.

BEST MODE FOR CARRYING OUT THE INVENTION

Figure 1:
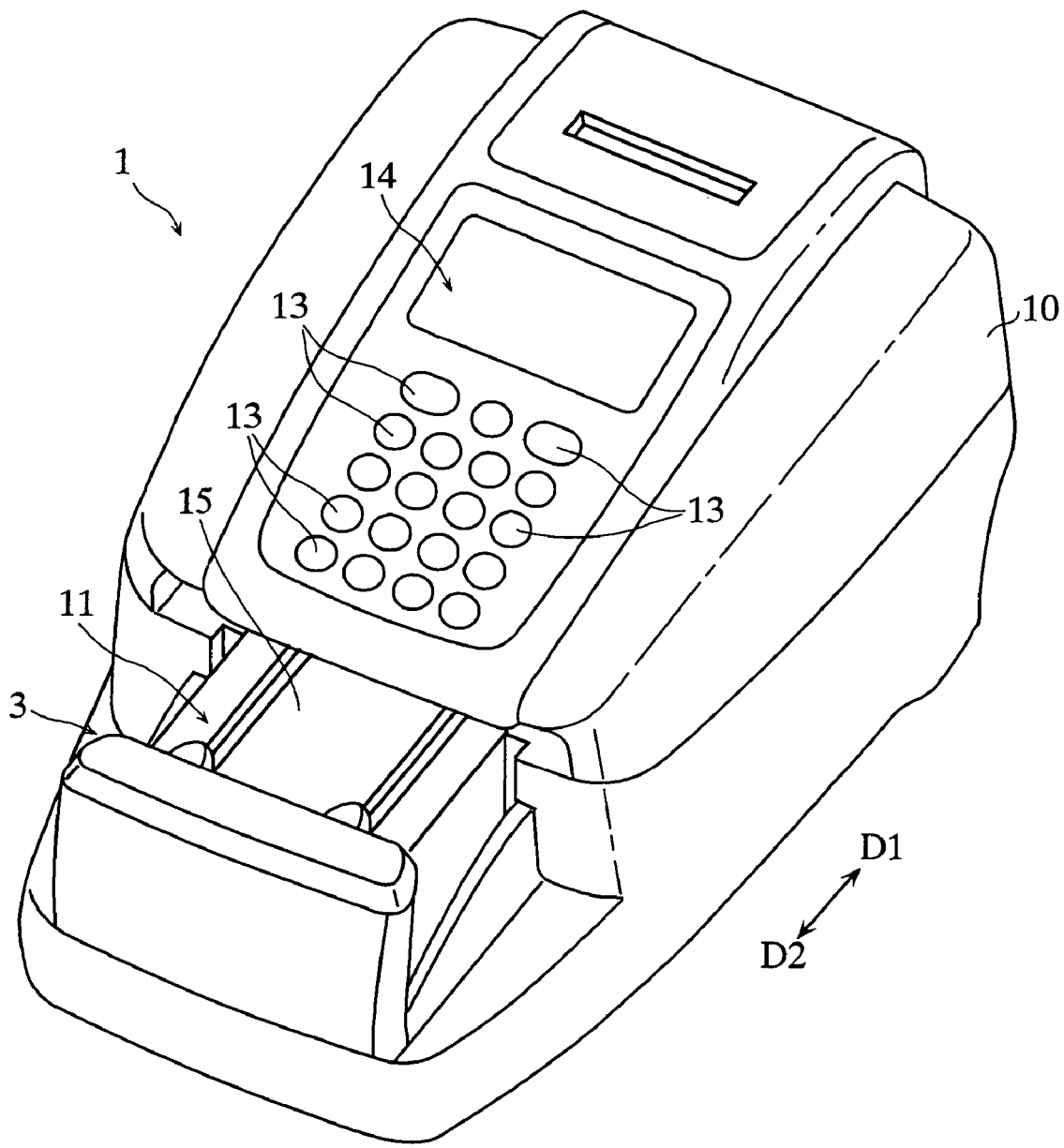
FIG. 1 is an overall perspective view of an analyzer according to the present invention.
Figure 2:
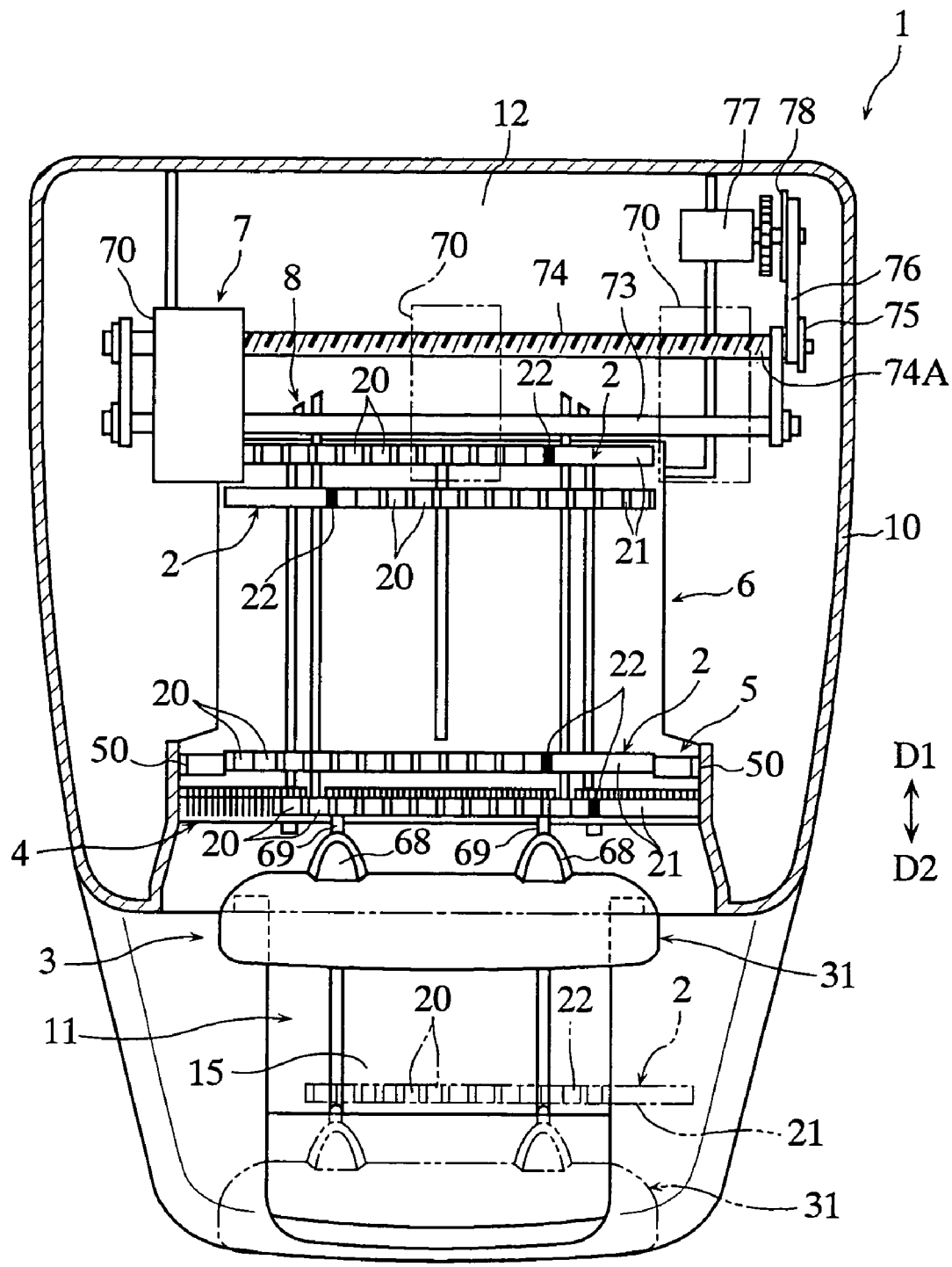
FIG. 2 is a sectional view for describing an internal configuration of the analyzer in FIG. 1.

An analyzer 1 shown in FIG. 1 and FIG. 2 makes use of a test piece 2, and performs semi-automatic analysis for a plurality of components in urine. Specifically, when using the analyzer 1, the test piece 90 which includes reagent pads 20 is wetted with urine and is placed by the user onto a placement part 11 of the analyzer 1, whereupon photometric urine analysis is performed automatically. The test piece 2 to be used in the analyzer 1 is provided by a strip of base material 21 formed, longitudinally thereof, with a row of reagent pads 20 and a black mark 22. Each reagent pad is impregnated with a reagent. In the test piece 2, the base material 21 is formed of a white resin for example. A dimension of the black mark 22 longitudinally of the base material 21 is smaller than a dimension of each reagent pads 20 longitudinally of the base material 21.

As shown in FIG. 2, the analyzer 1 includes a case 10, a test piece placement part 11 and a disposal box 12, as well as a sliding conveyer mechanism 3, an excess urine removal mechanism 4, a position correction mechanism 5, a pitching mechanism 6, a photometric measurement mechanism 7 and a breaker mechanism 8.

As shown in FIG. 1, the case 10 is provided with a plurality of operation buttons 13 and a display panel 14. Each of the operation buttons 13 is for use by the user to generate signals for performing various operations (such as analyzing operation and printing operation), or to make various settings (such as analysis conditions and a client ID). The display panel 14 displays results of the analysis, error messages as well as instructions and operation status at the time when settings are made.

As shown in FIG. 1 and FIG. 2, the test piece placement part 11 is a portion for placing the test piece 2 whose reagent pads 20 are wetted with urine. The test piece placement part 11 is provided in front of the operation panel 13, by exposing part of a table 15 in a space of the case, opened above and to the sides. Specifically, the test piece placement part 11 is open to the above and to the sides of the table 15, and the test piece 2 can be placed, with the row of reagent pads 20 in the test piece 2 laid in the right and left directions. Also, in the test piece placement part 11, placement may be made in whichever of two ways; with the black mark 22 in the test piece 2 being on the left-hand side (hereinafter called "left-hand positioning") and on the right-hand side (hereinafter called "right-hand positioning") with respect to the row of reagent pads 20.

Figure 9:
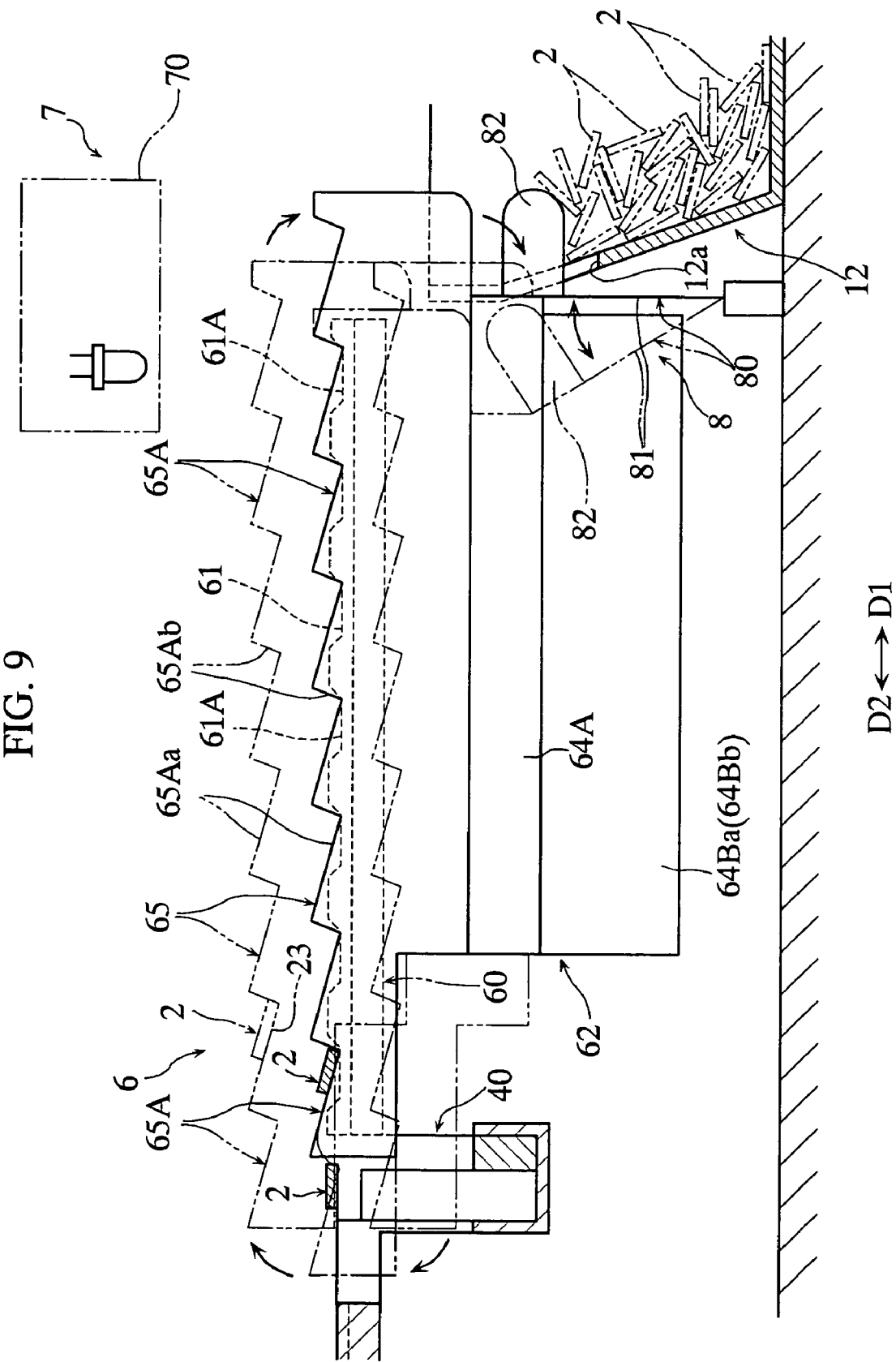
FIG. 9 is a perspective view for describing a pitching mechanism and a breaker mechanism of the analyzer in FIG. 1.
Figure 10:
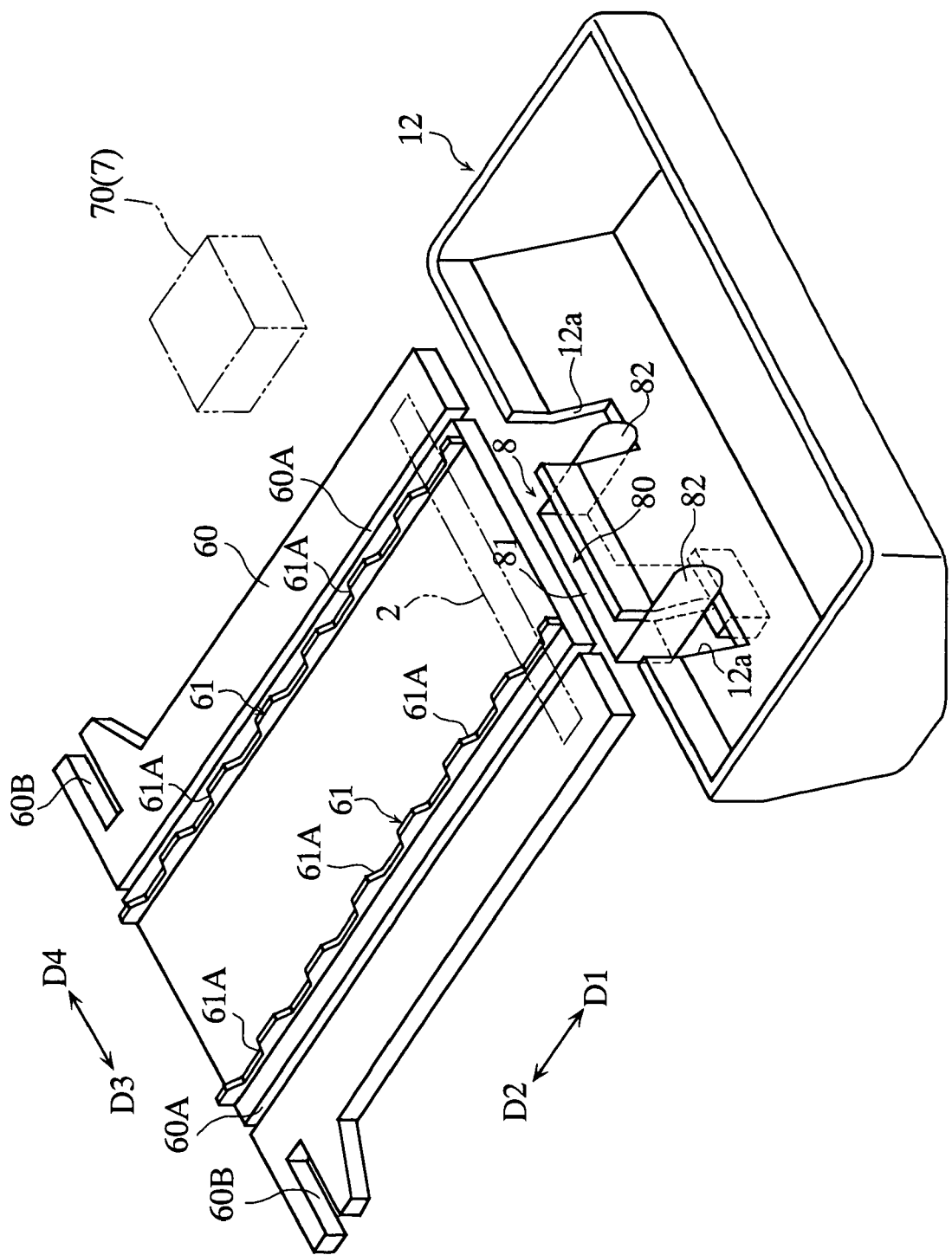
FIG. 10 is a perspective view for describing the pitching mechanism and the breaker mechanism of the analyzer in FIG. 1.

As shown in FIG. 2 and FIG. 9, the disposal box 12 which stores test pieces 2 after they are subjected to the photometric measurement is provided farther than the pitching mechanism 6. As shown in FIG. 9 and FIG. 10, the disposal box 12 is provided with a pair of cutouts 12a across a path for a rocking movement of pivoting paws 82 of a leaf spring member 80 in a breaker mechanism 8 which is to be described later.

Figure 3:
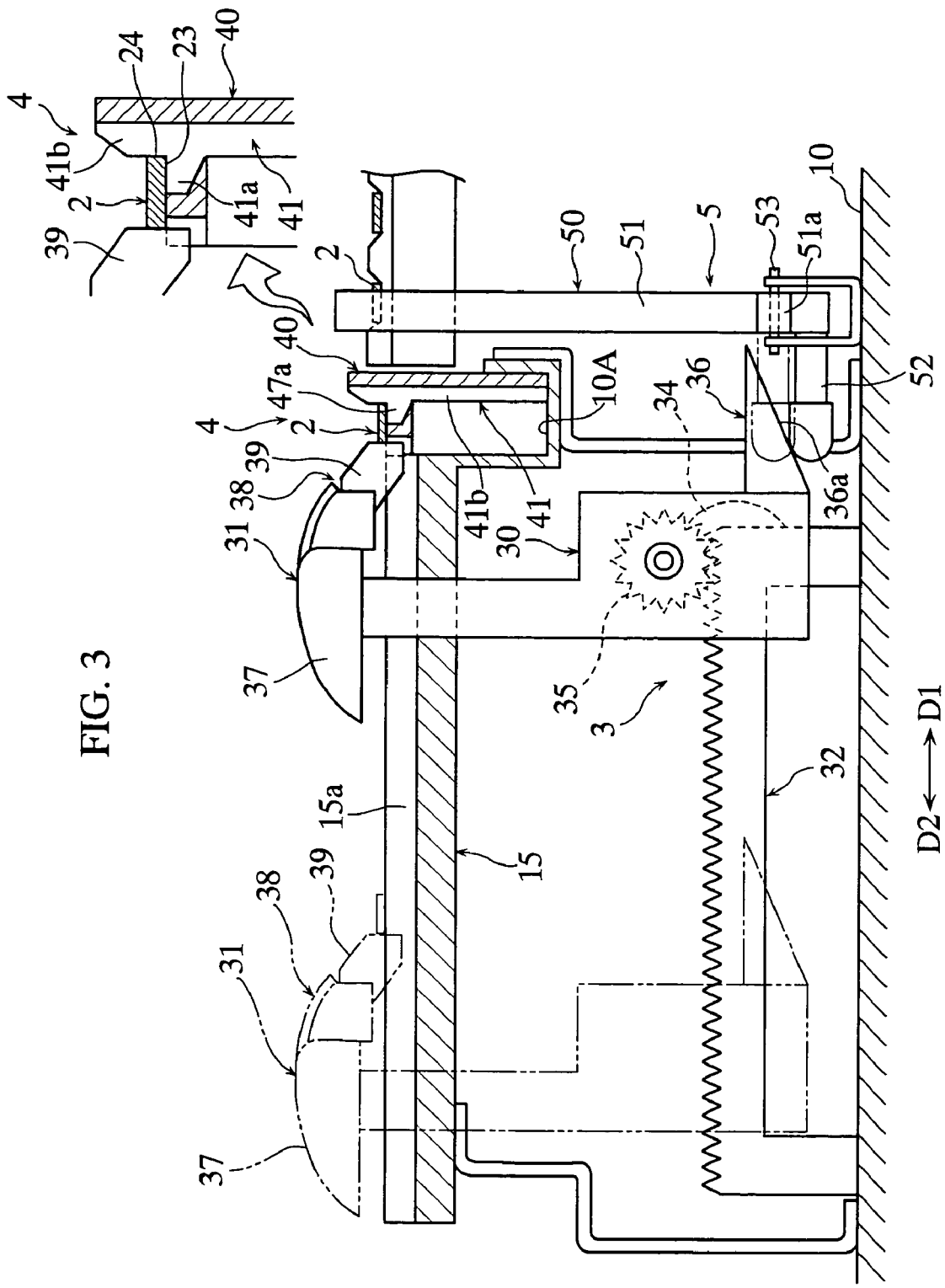
FIG. 3 is a sectional view of a primary portion, for describing a sliding conveyer mechanism in the analyzer in FIG. 1.
Figure 4:
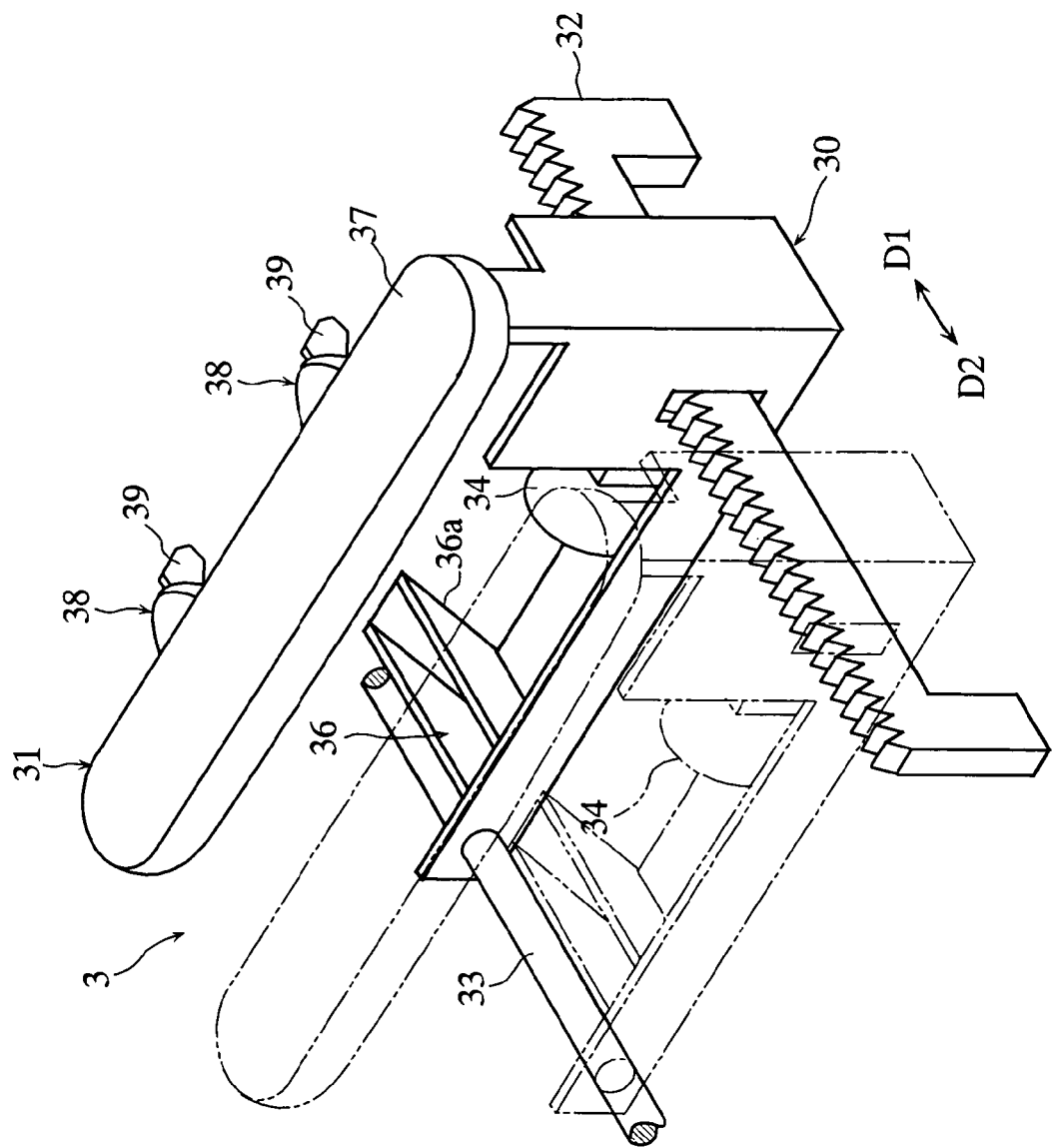
FIG. 4 is a perspective view showing elements of the sliding conveyer mechanism.

As shown in FIG. 2 through FIG. 4, the sliding conveyer mechanism 3 carries a test piece 2 placed on the test piece placement part 11 (table 15) to the excess urine removal block 40 of the excess urine removal mechanism 4 to be described later, and is provided with a carriage 30 and a pusher 31.

As shown in FIG. 3 and FIG. 4, the carriage 30 is supported below the table 15, by a rack 32 and a guide rod 33, for positive travel by a rack-and-pinion mechanism. More specifically, the carriage 30 is mounted with a motor 34, and driving force from the motor 34 is transmitted via a gear 35 to the rack 32 which is fixed to the case 10. In other words, the driving force from the motor 34 works on the rack 32 which is fixed to the case 10, and therefore works as a force to move the carriage 30 relatively to the rack 32. Thus, carriage 30 is able to make a reciprocating travel in directions indicated by Arrow D1 and D2, under a controlled drive from the motor 34 and a guide from the guide rod 33. The drive control of the motor 34 is provided by a controller 17 (See FIG. 14) to be described later. Further, the carriage 30 has a pair of interferers 36 extended in Direction D1. These interferers 36 have tapered surfaces 36a for making interference with interference counter portions 51 of pivoting members 50 in the position correction mechanism 5 which is to be described later.

On the other hand, the pusher 31 is connected with the carriage 30 so as to be above the table 15, and moves together with the carriage 30. Specifically, the pusher 31 makes a reciprocating travel in Directions D1, D2 when the carriage 30 is moved by a controlled drive from the motor 34. The pusher 31 includes a main body portion 37 formed with a pair of protrusions 38. Each of the protrusions 38 has a contact piece 39 for direct contact with a test piece 2. When the pusher 31 and the carriage 30 are moved, each contact piece 39 moves in a groove 15a provided in the table 15.

Figure 5:
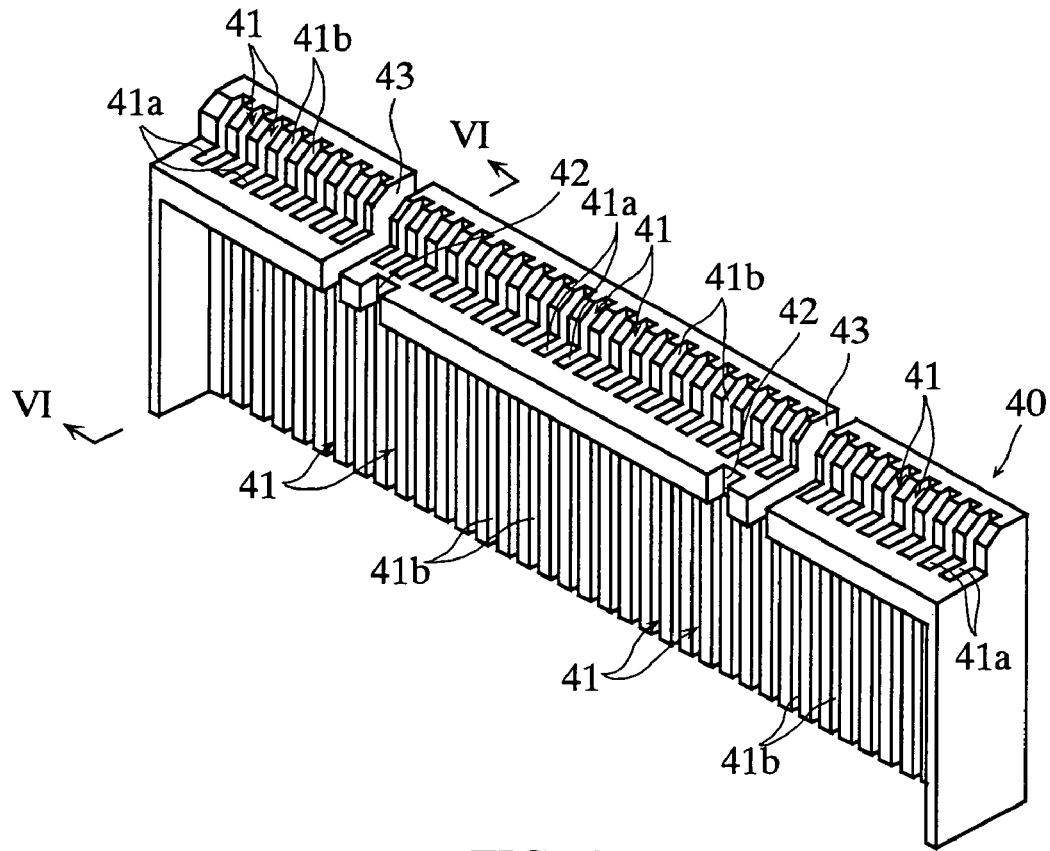
FIG. 5 is an overall perspective view showing an excess urine removal block in the analyzer in FIG. 1.

As shown in FIG. 3, the excess urine removal mechanism 4 has an excess urine removal block 40 for making contact with a test piece 2. The excess urine removal block 40 is attachable/detachable to and from a recess 10A formed in the case 10. As shown in FIG. 5, the excess urine removal block 40 has a plurality of grooves 41, a pair of first cutouts 42 and a pair of second cutouts 43.

As shown in FIG. 3 and FIG. 5, each groove 41 includes a first groove 41a and a second groove 41b. The first groove 41a which opens on the upper side allows a sucking force to act on a bottom surface 23 of a test piece 2. The second groove 41b which extends in up-and-down directions allows a sucking force to act on a side surface 24 of the test piece 2 while allowing urine removed from the test piece 2 to move downward.

As shown in FIG. 3, the pair of first cutouts 42 accept the contact pieces 39 of the pusher 31 when the pusher 31 presses a test piece 2 onto the excess urine removal block. Each of the first cutouts 42 is provided at a position corresponding to one of the grooves 15a in the table 15.

Figure 6:
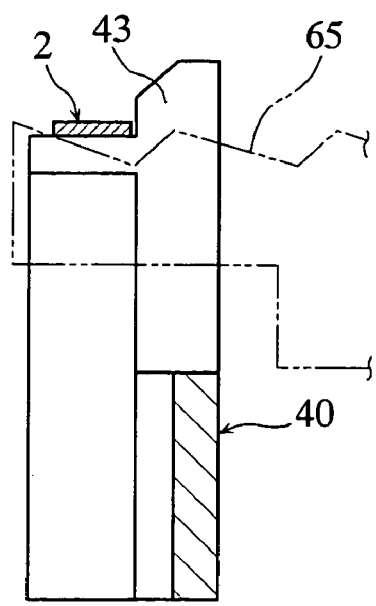
FIG. 6 is a sectional view taken in lines VI-VI in FIG. 5.

As shown clearly in FIG. 6, the pair of second cutouts 43 allow a rotating movement of a placement part 65 of a conveyer member 62 in the pitching mechanism 6 which will be described later.

Figure 7:
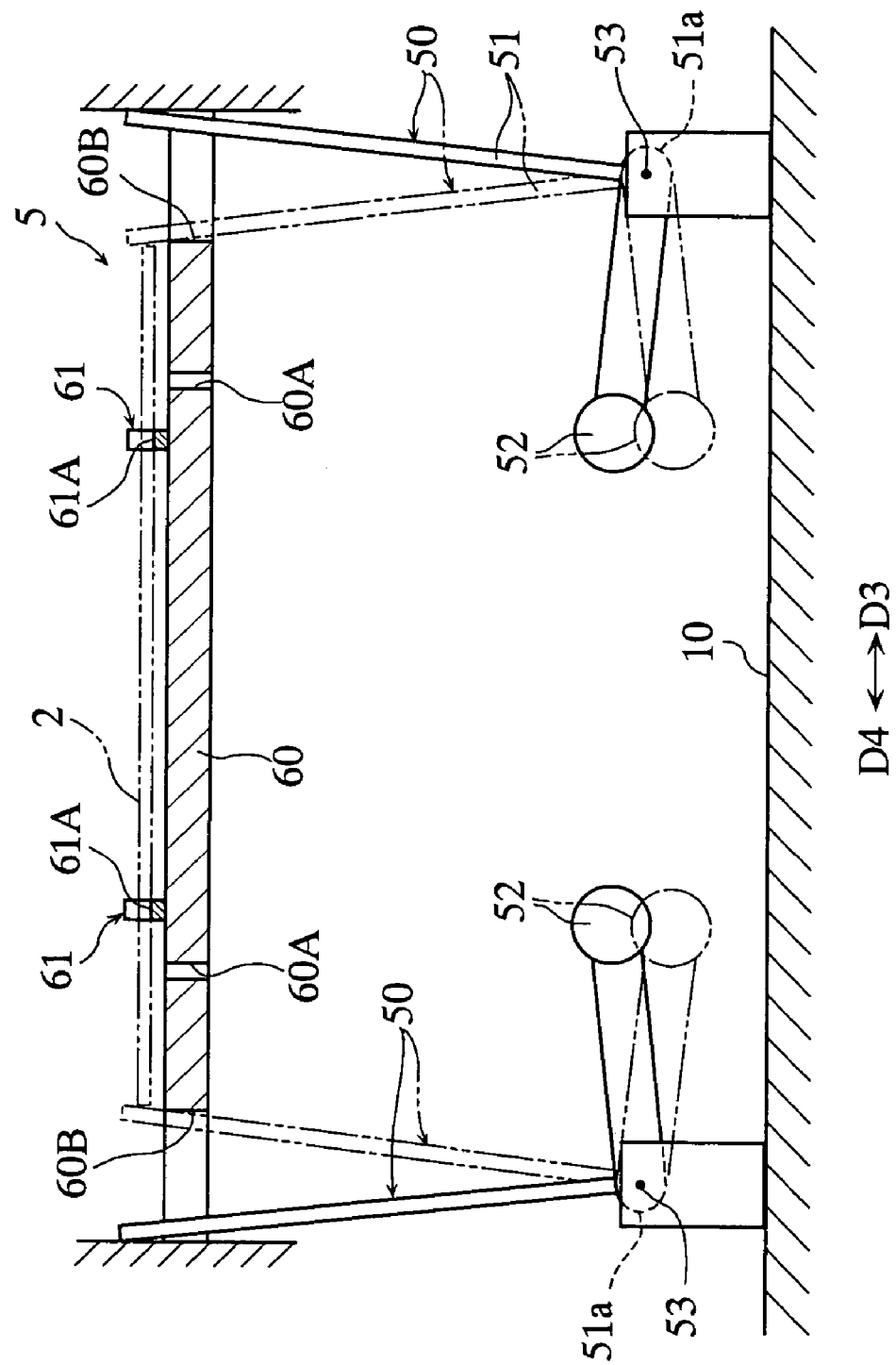
FIG. 7 is a sectional view of a primary portion, for describing a position correction mechanism in the analyzer in FIG. 1.
Figure 8:
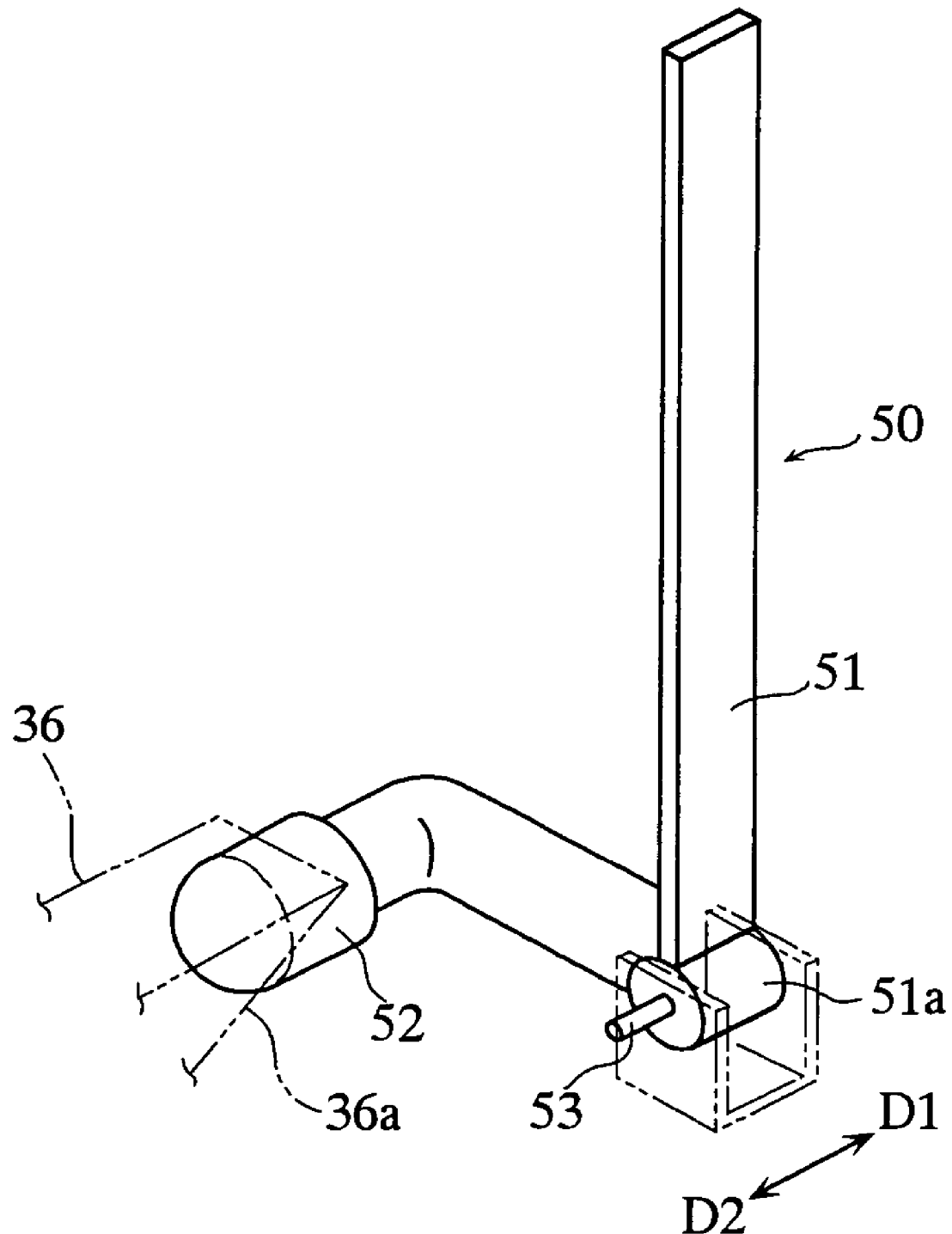
FIG. 8 is a perspective view showing a pivoting member of the position correction mechanism in FIG. 7.

As shown in FIG. 3 and FIG. 7, the position correction mechanism 5 corrects positional variation of a test piece 2 in Directions D3, D4, by holding the test piece 2 between a pair of pivoting members 50. As shown in FIG. 3, FIG. 7 and FIG. 8, each pivoting member 50 has a holding portion 51 and an interference counter portions 52, and is urged in a direction to move away from each other although this is not illustrated clearly in the figures. The holding portion 51 has an L-shape. The holding portion 51 is pivotably supported at a corner portion 51a via a shaft 52 with respect to the case 10 for a pivoting movement substantially in Directions D3, D4. The interference counter portions 52 are formed to protrude in Direction D2 from the holding portion 51, and are movable in up-and-down directions. The interference counter portion 52 is disposed on a travel path of the corresponding interferer 36 of the carriage 30. When the carriage 30 is moved in Direction D1 therefore, the interferer 36 interferes with the interference counter portion 52. Since the interferer 36 has the tapered surface 36a, part of the interferer 36 that interferes with the interference counter portion 52 is gradually displaced in Direction D2. As a result, after the interferer 36 makes the interference with the interference counter portions 52, the movement of the carriage 30 in Direction D1 will exert a downward force onto the interference counter portion 52, displacing the interference counter portion 52 in a downward direction. Thus, as shown clearly in FIG. 7, each holding portion 51 pivots to come closer to each other.

Figure 11:
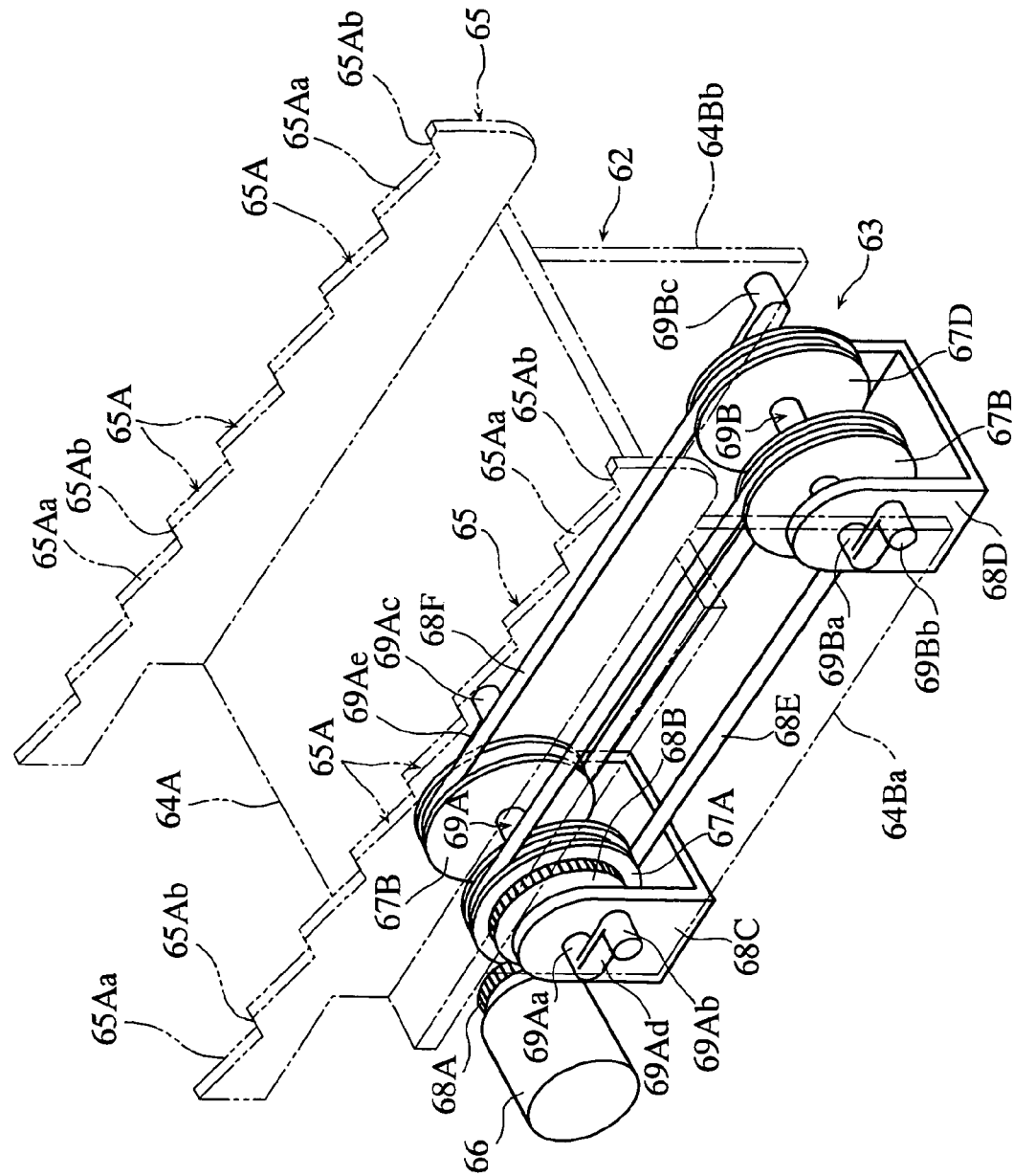
FIG. 11 is a sectional view for describing the pitching mechanism and a driving mechanism of the analyzer in FIG. 1.

As shown in FIG. 9, the pitching mechanism 6 conveys a test piece 2 on the excess urine removal block 40 (See FIG. 3) toward the disposal box 12 in a pitching movement. As shown in FIG. 9 through FIG. 11, the pitching mechanism 6 includes a conveyer table 60, a pair of rails 61, a conveyer member 62, and a driving mechanism 63.

As shown in FIG. 7 and FIG. 10, the conveyer table 60 provides conveying zone, and supports the rails 61. The conveyer table 60 is provided with a pair of slits 60A and a pair of cutouts 60B. The slits 60A allow a rotating movement of the placement part 65 (See FIG. 9) of the conveyer member 62 which will be described later, are spaced from each other by a predetermined distance, and extend in Directions indicated by Arrows D1, D2. On the other hand, the cutouts 60B allow a pivoting movement of the pivoting members 50 of the position correction mechanism 5.

The pair of rails 61 support the test piece 2, are spaced from each other in Directions indicated by Arrows D3, D4 by a predetermined distance, and extend in Directions D1, D2. Each rail 61 is provided with a plurality of recesses 61A in Directions D1, D2 as in the figure. The recesses 61A in each rail 61A are spaced from each other in Directions D1, D2 by a predetermined distance. The rails 61 supports a test piece 2 in parallel to Directions D3, D4. When the test piece 2 is supported by a pair of recesses 61A located on the most extreme side in Direction D2, the position correction mechanism 5 corrects positional variation of the test piece 2 in Directions D3, D4. On the other hand, when the test piece 2 is supported by a pair of recesses 61A located on the most extreme side in Direction D1, the photometric measurement mechanism 7 makes photometric measurement of the test piece 2.

As shown in FIG. 9 and FIG. 11, the conveyer member 62 conveys a test piece 2 placed on the rails 61 in pitching movement sequentially from a pair of recesses 61A to an adjacent pair of recess 61A. The conveyer member 62 makes a circular movement on a driving mechanism 63 (See FIG. 11) which will be described later. The conveyer member 62 has a pair of connecting plates 64Ba, 64Bb protruding downward from a supporting plate 64A, and a pair of placement part 65 protruding upward from the supporting plates 65A. The placement parts 65 are spaced from each other in Directions D3, D4, and to extend in Directions D1, D2 on the supporting plates 64A. Each placement part 65 has a plurality of cutouts 65A lined in Directions D1, D2. Each of the cutouts 65A in each placement part 65 has a pair of slanted surfaces 65Aa, 65Ab. A test piece 2 makes contact on its bottom surface 23, with the slanted surface 65Aa when the test piece 2 is conveyed.

As shown in FIG. 11, the driving mechanism 63 is to give a rotating movement to the conveyer member 62, and has a motor 66 and a first through a fourth pulleys 67A-67D.

The motor 66 which provides rotating force to the conveyer member 62 is connected with the first pulley 67A via gears 68A, 68B. In other words, the rotating force from the motor 66 is inputted to the first pulley 67A, i.e. the first pulley 67A is rotated by the motor 66. The motor 66 is controlled by the controller 17 (See FIG. 14) which will be described later.

The first through the fourth pulleys 67A-67D are rotatably supported on supporting brackets 68C, 68D. The first pulley 67A and the second pulley 67B are connected with each other via a belt 68E. Therefore, when the motor 66 rotates the first pulley 67A, the second pulley 67B rotates in the same direction as the first pulley 67A. The first pulley 67A is further connected with the third pulley 67C via a connecting member 69A. The connecting member 69A has a main shaft portion 69Aa and a first and a second sub shaft portions 69Ab, 69Ac.

The main shaft portion 69Aa is integral with and thus non-rotatable with respect to the first through the third pulleys 67A-67C, and is supported rotatably with respect to a supporting bracket 68C. In other words, when the first pulley 67A is rotated, the third pulley 67C rotates in the same direction as the first pulley 67A.

The first and the second sub shaft portions 69Ab, 69Ac are connected with the main shaft portion 69Aa via arm portions 69Ad, 69Ae. In other words, the first and the second sub shaft portions 69Ab, 69Ac are offset from the main shaft portion 69Aa as viewed from Direction D3 or D4. Therefore, the first and the second sub shaft portions 69Ab, 69Ac can revolve around the main shaft portion 69Aa. The first and the second sub shaft portions 69Ab, 69Ac are connected with the connecting plates 64Ba, 64Bb in the conveyer member 62. Therefore, rotating force of the first pulley 67A and the third pulley 67C can be used to rotate the connecting plates 64Ba, 64Bb.

The fourth pulley 67D is connected with the third pulley 67C via a belt 68F. Specifically, when the first pulley 67A turned and therefore the third pulley 67C is turned, rotating force of the third pulley 67C is transmitted to the fourth pulley 67D. Further, the fourth pulley 67D is connected with the second pulley 67B via a connecting member 69B. The connecting member 69B has, like the connecting member 69A which was described earlier: A main shaft portion 69Ba which is non-rotatable with respect to the second and the fourth pulleys 67B, 67D, and is rotatable with respect to the supporting bracket 68B; and a first and a second sub shaft portions 69Bb, 69Bc which are connected with the connecting plates 64Ba, 64Bb in the conveyer member 62. Therefore, when the first pulley 67A is turned thereby turning the second pulley 67B, rotating force of the second pulley 67B works to turn the fourth pulley 67D. Rotating force of the second and the fourth pulleys 67B, 67D works to rotate the connecting plates 64Ba, 64Bb.

In the driving mechanism 63 thus far described, rotating force of the motor 66 is inputted to the first pulley 67A, whereby the first through the fourth pulleys 67A-67D are rotated in the same direction, and rotating force of these pulleys 67A-67D works to rotate the connecting plates 64Ba, 64Bb (conveyer member 62), or more specifically, the placement part 65. As a result, the driving mechanism 63 can cause the placement part 65 to travel in a circular movement, under a control on the drive of the motor 66 provided by the controller 17 (See FIG. 14) which will be described later (See FIG. 14).

Figure 12:
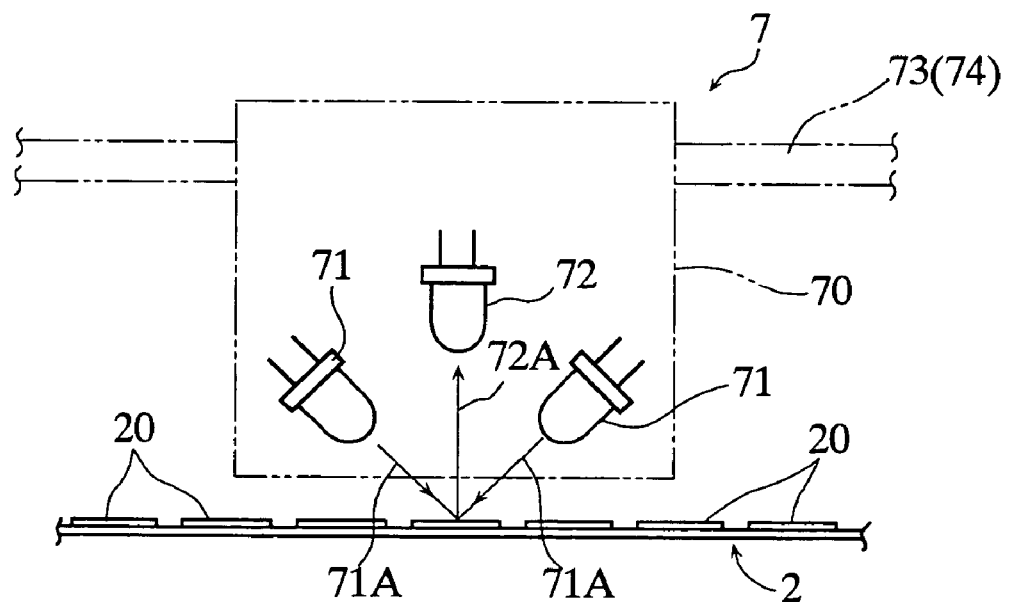
FIG. 12 is a partially transparent front view for describing a photometric measurement mechanism of the analyzer in FIG. 1.
Figure 13:
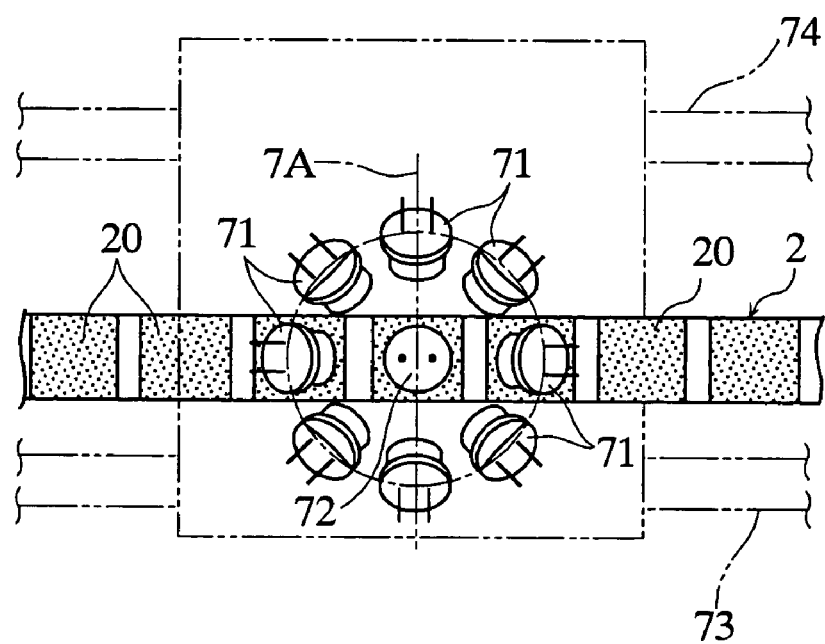
FIG. 13 a partially transparent front view for describing the photometric measurement mechanism in FIG. 12.

As shown in FIG. 2, FIG. 12 and FIG. 13, the photometric measurement mechanism 7 receives reflected light when each of the reagent pads 20 is irradiated, and obtains information represented by the degree of coloration in each reagent pad 20. The photometric measurement mechanism 7 has a plurality of light emitters 71 and an optical receiver 72 fixed within a holder 70. As shown in FIG. 2, the holder 70 is supported by the case 10 via the guide rod 73 and the screw 74. The screw 74, formed with a screw thread, is threaded into the holder 70 though not shown clearly in the drawings. The screw 74 has an end 74A to which a pulley 75 is attached. A belt 76 connects this pulley 75 with the pulley 78 which is attached to a motor 77. Specifically, rotating force of the motor 77 is transmitted to turn the screw 74, and by turning the screw 74, the holder 70 is traveled in Directions D3, D4.

As shown in FIG. 12 and FIG. 13, the light emitters 71 are able to emit light which has a specific peak wavelength for example, and are provided by LEDs. Each light emitter 71 is fixed to the holder 70, with the emitter's center axis of light 71A slanted by 45 degrees with respect to the horizontal surface (each reagent pad 20). On the other hand, the optical receiver 72, which receives the light reflected from each reagent pad 20, is provided by a photodiode for example. The optical receiver 72 is fixed to the holder 70, with the receiver's light reception center axis 72A being vertical. Specifically, the optical receiver 72 is configured to receive 45-degree scattering rays from the reagent pads 20, out of the light emitted from each light emitter 72 toward the reagent pads 20. As has been described earlier, the light emitters 71 and the optical receiver 72 are fixed to the holder 70. Therefore, the light emitters 71 and the optical receiver 72 travel together with the holder 70 when the holder 70 is moved.

The light emitters 71 are located in a circle, on the same circumference, with the optical receiver 72 positioned at the center. More specifically, the light emitters 71 are disposed in at least one of the following two patterns: A point symmetry with respect to the optical receiver 72; and line symmetry with respect to Line 7A which is a line passing the optical receiver 72 along the conveying direction D1 of the test piece 2. FIG. 13 gives an example of using six light emitters 71, with the light emitters 71 disposed in a circle at a 45-degree angular interval. Such a layout of the light emitters 71 in a point symmetry or a line symmetry with respect to the optical receiver 72 enables the optical receiver 72 to obtain the same light-reception data regardless of the right-handed placement or the left-handed placement of the test piece 2 on the test piece placement part 11.

Specifically, in the manufacturing process of the analyzer, dimensional tolerance in each of the parts and erection tolerance are unavoidable. For this reason, there is no guarantee that the test piece 2 will be conveyed horizontally, or the test piece 2 will be horizontal when placed on the position for processing by the photometric measurement mechanism 7. In a photometric measurement mechanism which only has a combination of a light emitter and an optical receiver, such a variation in the attitude (inclination) can cause an error which has a certain implication when a test piece 2 is set in the right-handed placement but has an opposite implication when the setting is made in the left-handed placement. For this reason, an analyzer which allows both of the right-handed placement and the left-handed placement, and has a photometric measurement mechanism provided only with a combination of a light emitter and an optical receiver is subjected to measurement error due to attitude variation (inclination) of the test piece 2. Additionally, in the photometric measurement mechanism 7, center axes of the light emitters 71 and optical receiver 72 can deflect when the holder 70 is moved. In general, the deflection caused by a travel to the right is different from the deflection caused by a travel to the left. In this case again, there is a problem which is similar to the problem caused by attitude variation (inclination) of the test piece 2: Here again, an analyzer which allows both of the right-handed placement and the left-handed placement, and has a photometric measurement mechanism provided only with a single combination of a light emitter and an optical receiver is subjected to measurement errors. As understood from the examples described above, there is a risk of measurement errors as described, under circumstances where positional variations of the test piece 2 or variations and deflection between the center axes of the light emitters 71 and optical receiver 72.

On the contrary, the photometric measurement mechanism 7 in the analyzer 1 has a combination of a single optical receiver 72 and a plurality of light emitters 71. Further, the light emitters 71 are laid in a specific relationship of a point symmetry or a line symmetry as described earlier. Therefore, when all of the light emitters 71 are lit simultaneously and the amount of reflected light in this condition is measured by the optical receiver 72, positive errors and negative errors offset each other, canceling the variations and deflection concerning the test piece 2 or center axes of the light emitters 71 and optical receiver 72, making possible to receive an equal amount of light in whichever mode of the right-handed placement and the left-handed placement. As a result, according to the photometric measurement mechanism 7, it becomes possible to avoid situation in which measurement result in the right-handed placement mode differs from measurement result in the left-handed placement mode. In other words, the photometric measurement mechanism 7 is not very much affected by positional variations of the test piece 2 or variations and deflection between the center axes of the light emitters 71 and optical receiver 72 and therefore, results obtained when the holder 70 is moved in the right-hand direction are the same as results obtained when the holder 70 is moved in the left-hand direction.

Positional variations of the test piece 2 or deflection between the axes of the light emitters 71 and optical receiver 72 can be a problem between different units of the same analyzer model. Specifically, due to dimensional tolerance in each of the parts and erection tolerance, there can be positional variations of the test piece 2 or variations and deflection between the center axes of the light emitters 71 and optical receiver 72 among a plurality of units of the same analyzer model. Further, even in a single unit of the analyzer 1, it is still likely that the test piece 2 will take difference attitude at each time of measurement. Even in these cases, it is possible, for the same reasons for the right-handed placement mode and the left-handed placement mode, to reduce variations among analyzers, or measurement variations in a single analyzer.

In the example shown in FIG. 13, the number of the light emitters 71 are six, and all the light emitters 71 are placed in a circle, on the same circumference, and are spaced at 45-degree interval; however, the layout pattern for the light emitters 71 may be selected in accordance with the number of the light emitters 71. For example, if three of the light emitters 71 are used, they should be laid at a 120-degree interval in a circle, and if four of the light emitters 71 are used, these light emitters 71 should be laid at a 90-degree interval in a circle.

As shown in FIG. 9 and FIG. 10, the breaker mechanism 8 is to reduce the tendency for the test piece 2 to pile up at a single spot as they are stored in the disposal box 12, and the mechanism has a leaf spring member 80. The leaf spring member 80 has a T-shaped portion 81, from which a pair of paws 82 protrude in Direction D1. As shown in FIG. 9, the leaf spring member 80 is urged in Direction D2, fitted to the supporting plates 64A of the conveyer member 62, and fixed to the case 10, by a lower end of the T-shaped portion 81. Specifically, the leaf spring member 80 is fitted to the supporting plates 64A even when the conveyer member 62 is making a circular movement, and is rocked by the circular movement of the conveyer member 62. As has been described earlier, the disposal box 12 is provided with a pair of cutouts 12a across the rocking path of the paws 82. Therefore, when the conveyer member 62 (supporting plates 64A) is displaced in Direction D1, and the leaf spring member 80 is pivoted in Direction D1, the paws 82 protrude through the cutouts 12a, into the disposal box 12 (a state in which the leaf spring member 80 takes a position as illustrated in solid lines in FIG. 9). On the other hand, when the conveyer member 62 (supporting plates 64A) is displaced in Direction D2 and the leaf spring member 80 is pivoted in Direction D2, the paws 82 does not protrude into the disposal box 12 (a state in which the leaf spring member 80 takes a position as illustrated in phantom lines in FIG. 9). Specifically, in the breaker mechanism 8, selection is made for the state in which the paws 82 protrude into the disposal box 12 or the state in which the paws 82 do not, as the conveyer member 62 (supporting plates 64A) makes the circular movement.

Figure 14:
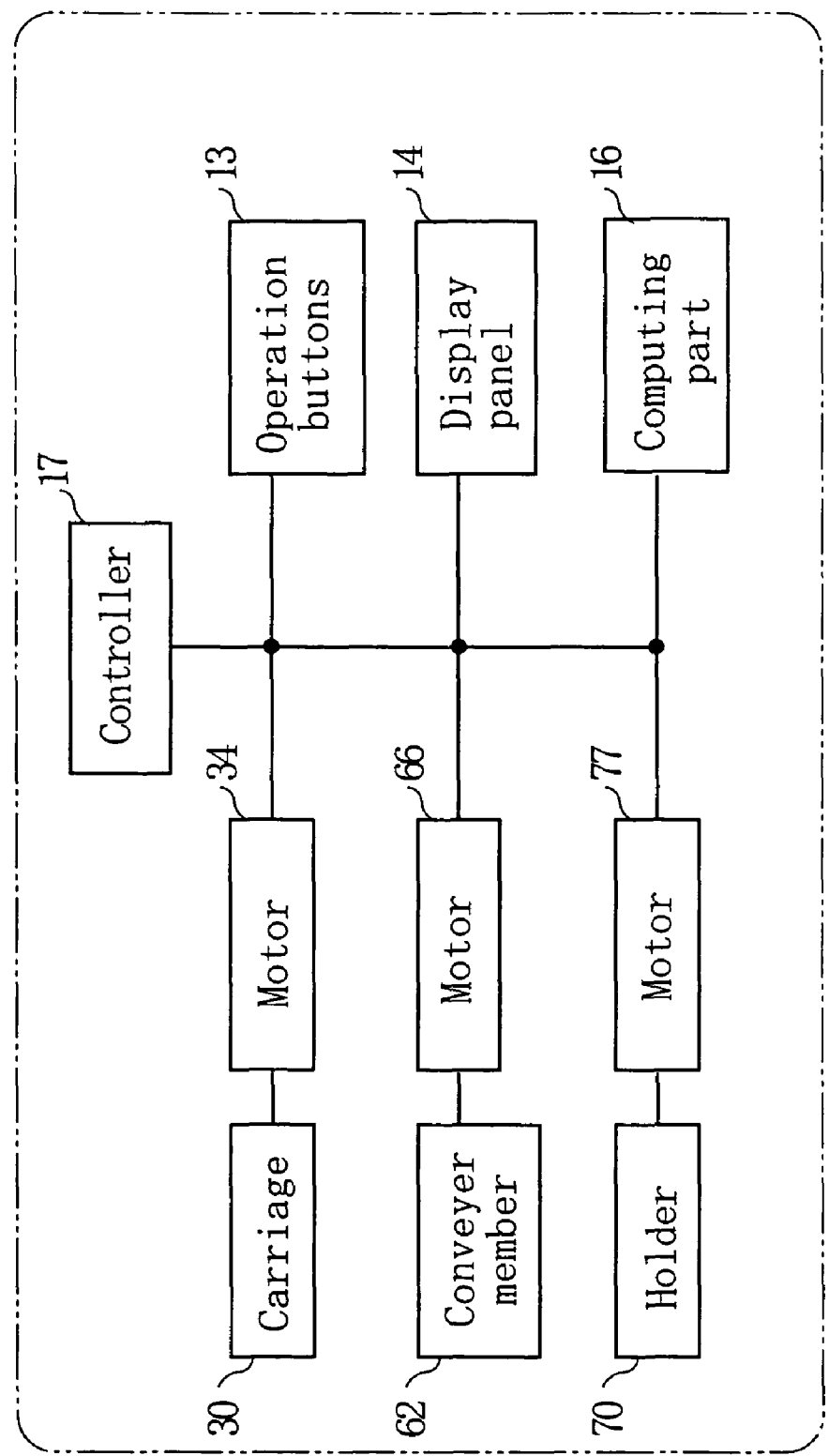
FIG. 14 is a block diagram for describing the analyzer in FIG. 1.

As shown in FIG. 14, the analyzer 1 further includes, in addition to those elements which are described above, a computing part 16 and a controller 17. These elements can be provided by a combination of a CPU, a RAM and a ROM for example.

Figure 15:
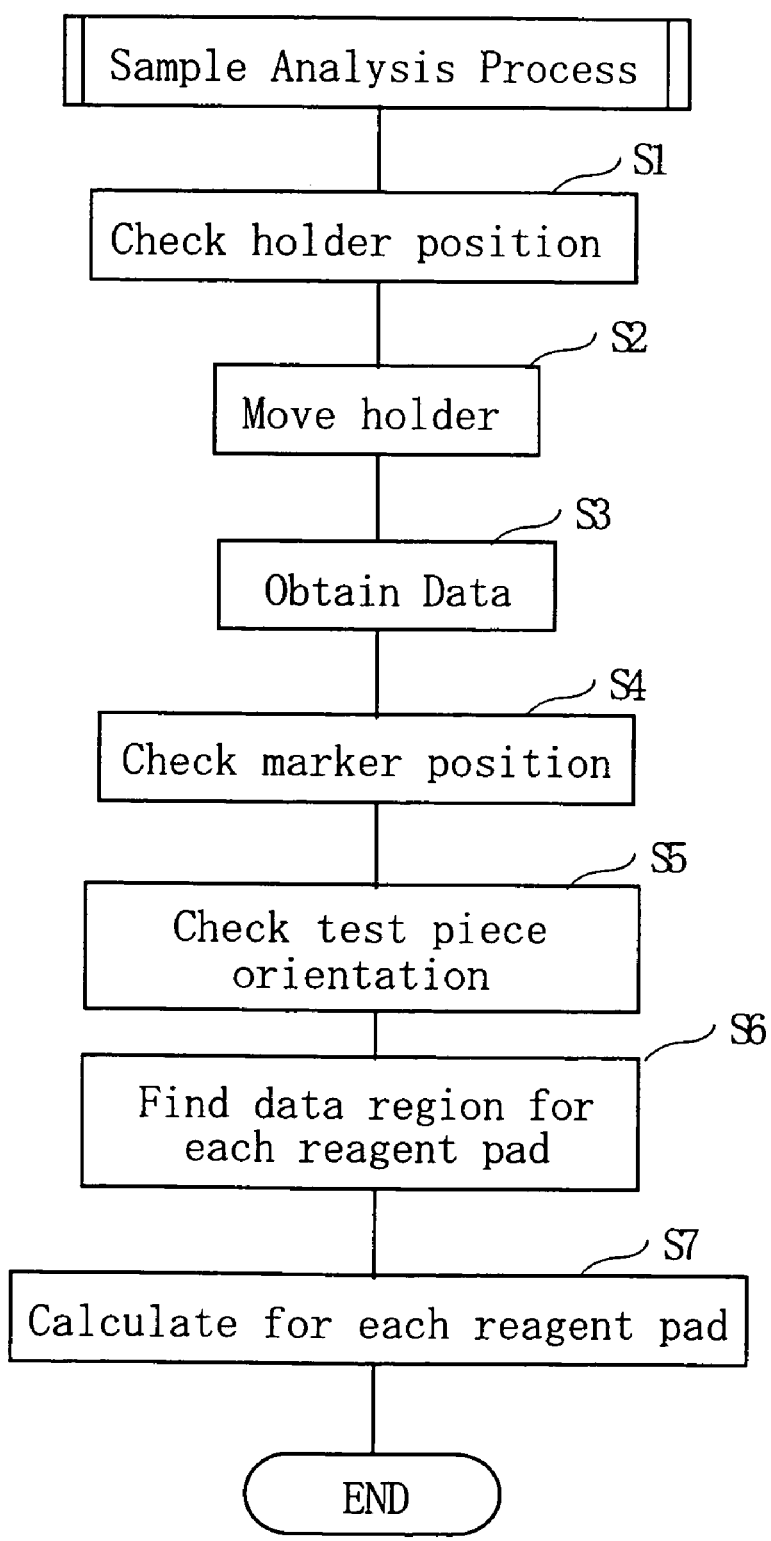
FIG. 15 is a flowchart for describing an operation of a computing part in FIG. 14.

The computing part 16 calculates the concentration of a specific component in urine, based on results of light reception at the optical receiver 72 of the photometric measurement mechanism 7, and following a procedure (See FIG. 15) which will be described later.

The controller 17 controls each of the elements. Typically, the controller 17 controls the drive of the motor 34, thereby controlling the reciprocating movement of the carriage 30 (pusher 31 (See FIG. 3)), controls the drive of the motor 66, thereby controlling the circular movement of the conveyer member 62 (placement part 65 (See FIG. 11)), and controls the drive of the motor 77, thereby controlling the reciprocating movement of the holder 70 (light emitters 71 and optical receiver 72 (See FIG. 12)).

Next, an analyzing operation in the analyzer 1 will be described, taking a case where test pieces 2 are placed continually onto the test piece placement part 11 and continuous analysis is performed on the test pieces 2.

In the analyzer 1, upon operation of a specific operation button 13 for example, each of the motors 34, 66 are driven to drive the carriage 30 (pusher 31) in a reciprocating movement, and the conveyer member 62 (placement part 65) in a circular movement under, the control provided by the controller 17.

As clearly shown in FIG. 2 and FIG. 3, in the sliding conveyer mechanism 3, the pusher 31 starts its travel in Direction D1 from a stand-by position on the side of Direction D2, to face the excess urine removal block 40, and then brought in Direction D2 back to the stand-by position. At the stand-by position, the pusher 61 is stopped for a predetermined period of time. Specifically, the pusher 31 is controlled to repeat a reciprocating movement intermittently through the drive of the motor 34 under the control provided by the controller 17 (See FIG. 14).

Meanwhile, the user can place a test piece 2 onto the test piece placement part 11 while the pusher 31 is staying in the stand-by position. As has been described, the test piece placement part 11 is open on the upper side and on the right and left sides (See FIG. 1), so it is possible to place the test piece 2 onto the piece placement part 11 in whichever way of the right-handed placement and the left-handed placement. Thus, according to the analyzer 1, whether the user uses his right hand or left hand, he can easily place the test piece 2 onto the test piece placement part 11 regardless of which hand he uses. Hence, according to the analyzer 1, it is possible, regardless of the user's dominant hand or the position to place the urine container, to place the test piece 2 onto the test piece placement part 11 very easily. Also, the user should simply place the test piece 2 so that the reagent pads 20 lie in Directions D3, D4 on the test piece placement part 11. In this arrangement, the motion required of the user for placing the test piece 2 is smaller than the case where the test piece 2 must be placed so that the reagent pads 20 lie in Direction D1, D2 and therefore, the motion for placing the test piece 2 onto the test piece placement part 11 is easy.

The test piece 2 which was placed on the test piece placement part 11 is pushed and moved by the contact pieces 39 of the pusher 31 when the pusher 31 moves in Direction D1, to a position faced by the excess urine removal block 40, and is pressed by the pusher 31 (contact pieces 39) onto the excess urine removal block 40. This corrects positional variation of the test piece 2 in Directions D1, D2, making the test piece perpendicular to the conveying direction D1.

As shown clearly in FIG. 3, when the test piece 2 is pressed by the pusher 31 onto the excess urine removal block 40, the first grooves 41a of the excess urine removal block 40 are sealed by the bottom surface 23 of the test piece 2. This causes the first grooves 41a to introduce a sucking force on the bottom surface 23 of the test piece 2, removing excess urine from the bottom surface 23 of the test piece 2. Meanwhile, a side surface 24 of the test piece 2 receives a sucking force from the second grooves 41b of the excess urine removal block 40, so excess urine is removed from the side surface 24 of the test piece 2.

Meanwhile, as shown in FIG. 9, the pitching mechanism 6 is in motion as has been described earlier: The conveyer member 62 i.e. the placement part 65 is in a circular movement. As will be anticipated from FIG. 9 and FIG. 10, the circular movement of the placement part 65 is controlled in such a way that a test piece 2 which has been brought to the excess urine removal block 40 and is in contact with the excess urine removal block 40 will be transferred to the conveyer table 60 (more specifically on a pair of recesses 61A in the rails 61 on the most extreme side in Direction D2) by the time when the next test piece 2 is brought to the excess urine removal block 40. Therefore, when test pieces 2 are supplied continually to the excess urine removal block 40, the pitching mechanism 6 will move these test pieces 2 continually to the conveyer table 60 (recesses 61A).

As shown clearly in FIG. 7, once the test piece 2 is brought to the conveyer table 60 (recesses 61A), the position correction mechanism 5 corrects positional variation in Directions D3, D4. As shown in FIG. 3 and FIG. 7, in the position correction mechanism 5, a travel of the carriage 30 in Direction D1 brings the interferers 36 of the carriage 30 into interference with the interference counter portions 52 of the pivoting members 50 in the position correction mechanism 5. This pivots the pivoting members 50, bringing the pair of holding portions 51 closer to each other. Therefore, the test piece 2 on the recesses 61A is sandwiched between the holding portions 51, and positional variation in Directions D3, D4 is corrected as the carriage 30 moves in Direction D1 and the pivoting members 50 pivot to come closer to each other.

According to the analyzer 1, positional variation correction to a test piece 2 in Directions D3, D4 is achieved in a repeating cycle as the pair of pivoting members 50 in the position correction mechanism 5 are pivoted. Specifically, according to the position correction mechanism 5, positional variation correction to a test piece 2 in Directions D3, D4 is not performed while the test piece 2 is traveling over a predetermined distance: Rather, positional variation correction to a test piece 2 in Directions D3; D4 is performed at a specific location. Therefore, in the analyzer 1, it is not necessary to secure a long distance in Directions D1, D2 in order to provide a correction zone for making positional variation correction to a test piece 2 in Directions D3, D4. As a result, according to the analyzer 1, it is possible to make positional variation correction to a test piece 2 in Directions D3, D4 without increasing the size of the analyzer in Directions D1, D2.

As anticipated from FIG. 9, after the positional correction in Directions D3, D4, the test piece 2 is pitched further as it is moved to the next pair of recesses 65 in the next pitch in the circular movement of the placement part 65 in the pitching mechanism 6.

More specifically, first, the test piece 2 on the recesses 61A is held up by the cutouts 65A of the placement part 65 when the cutouts 65A pass over the recesses 61A of the rails 61 from below to above the conveyer table 62. During this lifting motion, the weight of the test piece 2 makes the piece sit at the deepest position on the cutouts 65A and be fitted to the slanted surfaces 65Aa. Therefore, the parallelism of the test piece 2 to Directions D3, D4 is maintained when lifted. Next, after the cutouts 65A of the placement part 65 have passed between the rails 61 in an upward direction along an arc path, the test piece 2 is passed from the cutouts 65A to a corresponding pair of the recesses 61A when the cutouts 65A of the placement part 65 pass that pair of recesses 61A in a downward direction from above to below the rails 61. This cycle of lifting the test piece 2 from the recesses 61A and transferring the test piece 2 from the cutouts 65A to the recesses 61A as described above is repeated in the circular movement of the placement part 65. Thus, a test piece 2 on the most extreme pair of recesses 61A in the rails 61 in Direction D1 is brought for photometric measurement by the photometric measurement mechanism 7, and then is moved to the disposal box 12 in the next cycle of circular movement by the placement part 65.

The disposal box 12 receives test pieces 2 one after another, after they undergo photometric measurement. Since the disposal of the test pieces 2 is made by the pitching mechanism 6 in the circular movement of the placement part 65, the test pieces piles up at one place.

However, the analyzer 1 is provided with the breaker mechanism 8. Specifically, in association with the circular movement of the placement part 65, the leaf spring member 80 is rocked, repeating a cycle of a state where the paws 82 of the leaf spring member 80 protrude into the disposal box 12 and a state they do not. Thus, if there is a large pile of test pieces 2 in the disposal box 12, the paws 82 will interfere with the pile of test pieces 2 when protruding into the disposal box 12. As a result, the pile of test pieces 2 is broken down in the disposal box 12, by the breaker mechanism 8. Further, due to the repetitive protruding movement of the paws 82 into the disposal box 12 provided by the circular movement of the placement part 65, the pile of test pieces 2 in the disposal box 12 will not grow beyond a certain height, eliminating a possibility that a grown pile of test piece will interfere with other elements such as the photometric measurement mechanism 7 to cause analysis errors. Also, when a pile of test pieces 2 is broken down, test pieces 2 which were in the broken portion of the pile will find their way to empty spaces in the disposal box 12. As a result, storage space in the disposal box 12 is now used effectively. This eliminates a need for securing a large height dimension for the disposal box 12, a need for a more sophisticated conveying mechanism or a need for a complicated configuration of the disposal mechanism, in the analyzer 1. Therefore, the analyzer 1 enables to eliminate undesirable piling up of test pieces in the disposal box 12, without increasing the size of the analyzer nor increasing the cost of manufacture.

Now, as will be anticipated from FIG. 2, photometric measurement takes place in the photometric measurement mechanism 7 while the holder 70 is being moved in Direction D3 or Direction D4. Results of light reception at the optical receiver 72 (See FIG. 12 and FIG. 13) of the photometric measurement mechanism 7 are sent to the computing part 16 shown in FIG. 14, where analysis of a specific component in urine takes place in the computing part 14. Such a sequence of sample analysis as the above, including photometric measurement and calculation, may follow steps shown in a flowchart in FIG. 15 for example.

In the sample analysis process in the analyzer 1, first, the computing part 16 in FIG. 14 checks the position of the holder 70 (S1). Specifically, identification is made for whether the holder 70 is at a left-hand side stand-by position (shown in solid lines in FIG. 2) or at a right-hand side stand-by position (shown in phantom lines in FIG. 2). Position identification such as this can be performed using e.g. photo-interrupters placed at the left-hand side stand-by position and the right-hand side stand-by position thereby detecting the presence of the holder 70, or keeping memory of the direction, i.e. whether the holder 70 was last moved to the right or to the left before the holder 70 was brought to the present position.

Figure 16:
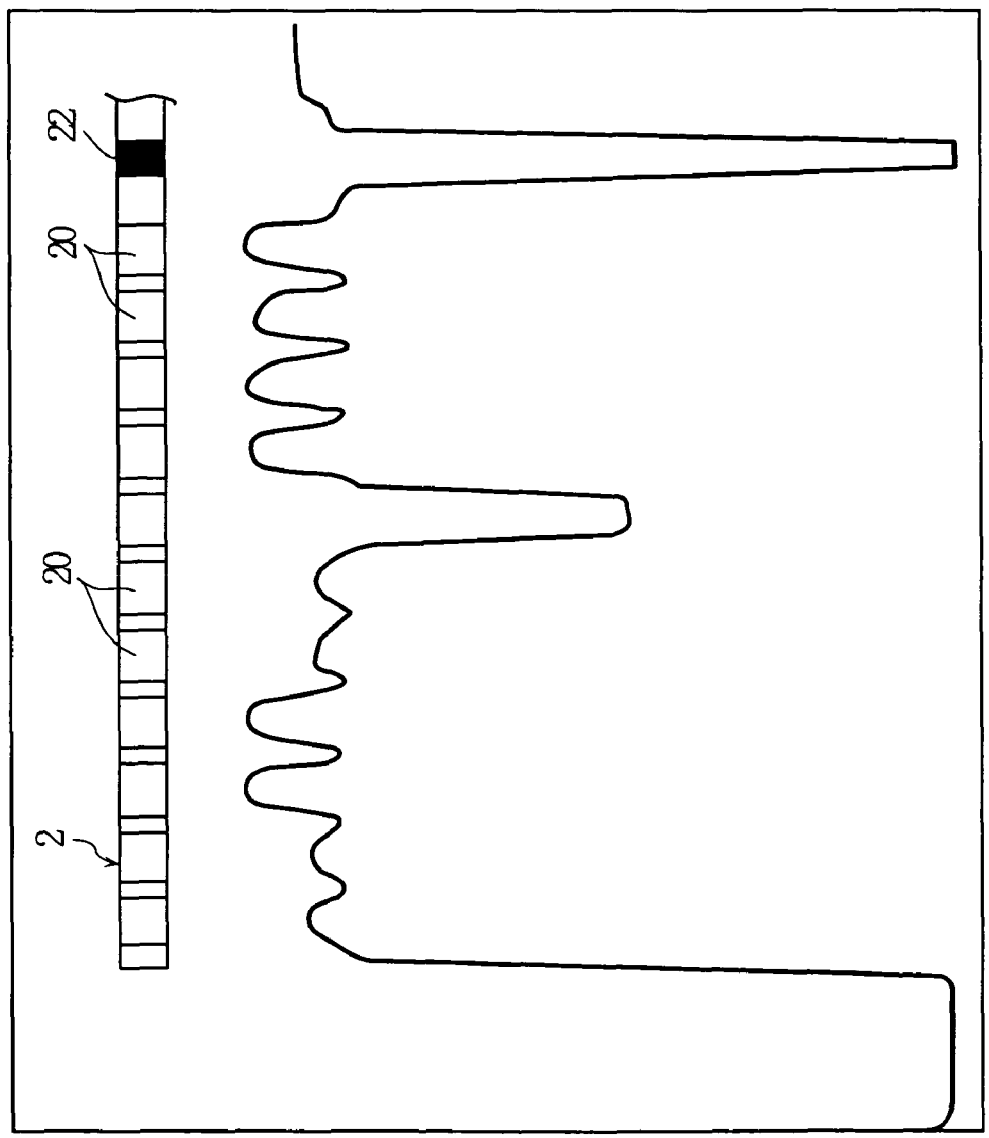
FIG. 16 is a graph showing an example of data obtained by an optical receiver of the photometric measurement mechanism shown in FIG. 12 and FIG. 13.

Next, the controller 17 in FIG. 14 moves the holder 70 to the left if it is at the right-hand side stand-by position until it reaches the left-hand side stand-by position, or to the right if the holder 70 is at the left-hand side stand-by position until it reaches the right-hand side stand-by position (S2). The moving direction of the holder 70 is memorized at the computing part 16 for example. The holder 70 is moved while the placement part 65 of the conveyer member 62 is below the cutouts 61A of the rails 61 (See FIG. 9). During this step, the computing part 16 obtains data necessary for the sample analysis (S3), through light emission from the light emitters 71 to the reagent pads 20 on the test piece 2 and light reception by the optical receiver 72. An example of the data obtained by the computing part 16 is shown in FIG. 16. Specifically, reflected light from a region formed with the black mark 22 on the test piece 2 has a reflectance (light reception amount) smaller than a threshold and has a peak waveform region of a predetermined width, whereas reflected light from any of the reagent pads 20 has a reflectance (light reception amount) representing the degree of coloration of the reagent pad 20 and has a peak waveform region of a predetermined width.

In the computing part 16 in FIG. 14, the position of the black mark 22 on the test piece 2 is identified on the basis of the light reception results in step S3, with the moving direction of the holder 70 taken into consideration (S4). More specifically, first, the obtained data is searched for a peak portion whose reflectance (light reception amount) is not grater than the threshold value. The black mark is considered to be in this portion. The threshold value is, for example, a value which is smaller than an assumed minimum value of the reflectance (light reception amount) of the reagent pad 20. Alternatively, the position of the black mark 22 can be identified by checking the width of the peak waveform. Specifically, the test pieces 2 illustrated in the drawings have their black mark narrower than the width of any reagent pads 20; therefore, the position of the black mark 22 can be identified by finding a peak waveform which has a small width.

Next, the computing part 16 identifies the orientation of the test piece 2 (S5). The orientation of the test piece 2 can be identified by e.g. checking time course changes in the obtained data, taking into account the moving direction of the holder 70, to see if the peak waveform region which represents the black mark 22 appears before or after a chain of peak waveform regions which represents the reagent pads 20.

Further, in the computing part 16, identification is made for a data region (peak waveform region) for each of the reagent pads 20 (S6). The identification of the data regions is achieved on the basis of the information obtained in steps S3 through S5, by finding a match with the black mark 22 and with each of the reagent pads 20 on the test piece 2 in the time course change of the obtained data.

Next, the computing part 16 makes calculation necessary for the analysis for each reagent pad thereby making analysis of a specific component assigned to each reagent pad 20 (S7). More specifically, in step S6, the computing part 16 takes a peak value of the reflectance (light reception amount) from each data region which is already related to a specific one of the reagent pads 20. Each peak value is interpreted by using a predetermined analytical curve, into a concentration value of the specific component contained in the sample. Results of the calculation are displayed on the display panel 14 for example, to let the user know the analysis results.

According to the analyzer 1, the holder 70 does not have to make a reciprocating trip in Directions D3, D4, but rather the holder 70 makes a one-way trip from one stand-by position to the other stand-by position for photometric measurement of a test piece 2, and calculations necessary for the sample analysis is performed by the computing part 16 based on the photometric measurement. Specifically, according to the analyzer 1, it is possible to halve the travel distance necessary for the holder 70 to make a cycle of photometric measurement, of the case where the holder 70 must make a reciprocating trip for the photometric measurement. Therefore, according to the analyzer 1, it becomes possible to shorten photometric measurement time and thereby increase the speed of sample analysis. Also, by shortening the travel distance necessary for the holder 70 to make a cycle of photometric measurement, and thereby reducing wear and tier of the drive mechanism of the holder 70, it becomes possible to increase the life.

Figure 17:
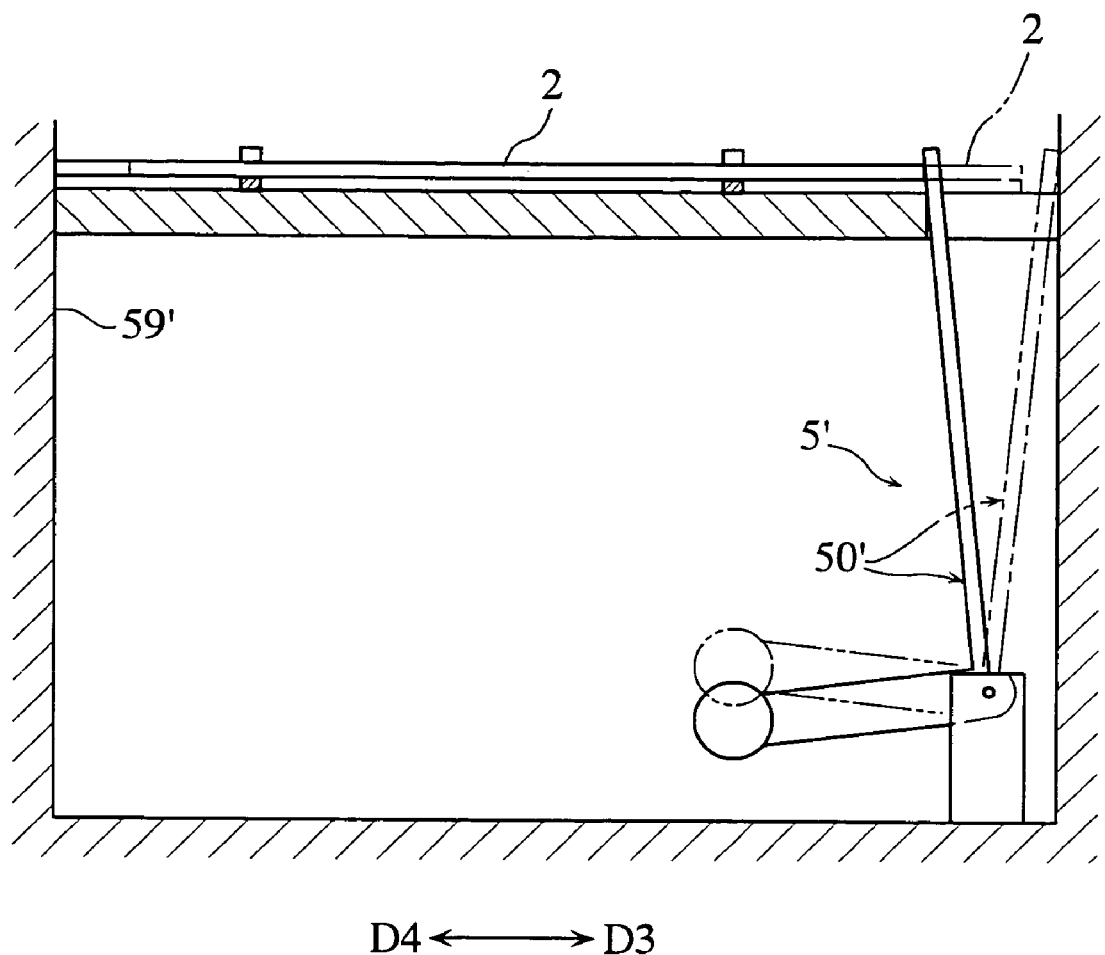
FIG. 17 is a sectional view for describing another example of the position correction mechanism.
Figure 18:
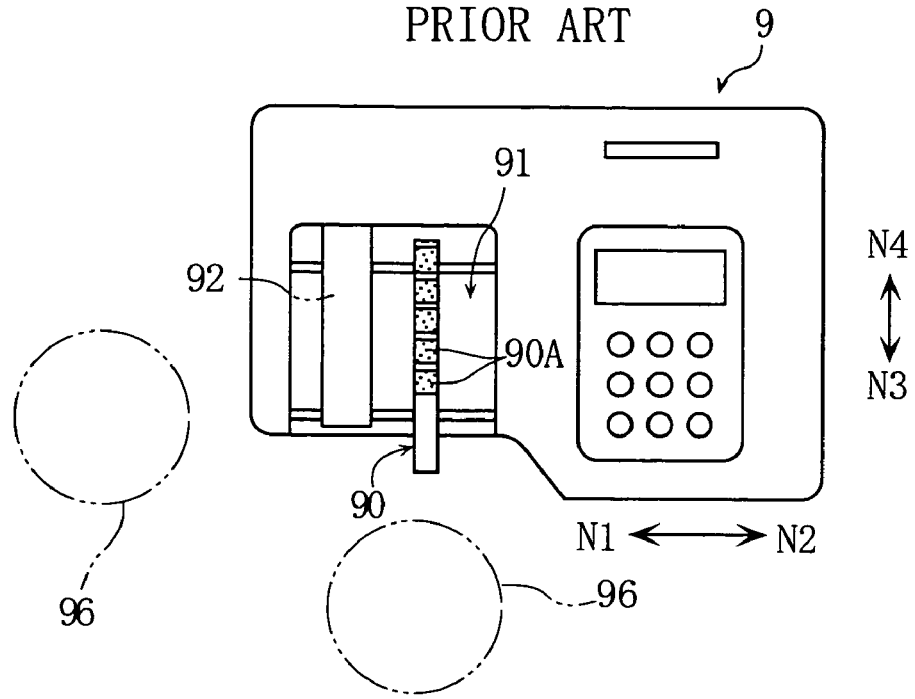
FIG. 18 is a plan view for describing a conventional analyzer.
Figure 19:
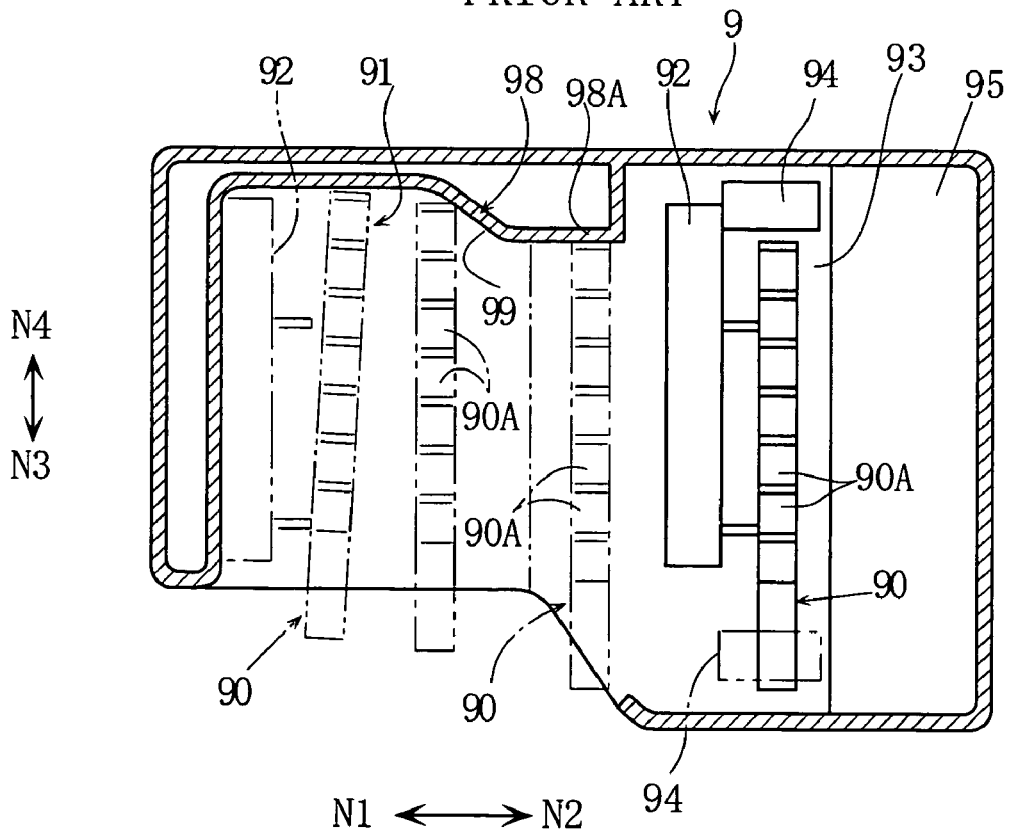
FIG. 19 is a partially exposed plan view of the analyzer in FIG. 18.

The present invention is not limited to the embodiment described above, and may be varied in many ways. For example, the position correction mechanism 5 does not necessarily include a pair of pivoting members 50. Specifically, As shown in FIG. 17, a position correction mechanism 5' may include a pivoting member 50', so that position correction of a test piece 2 in Directions D3, D4 may be achieved by holding a test piece 2 between the pivoting member 50' and a wall surface 59'. As another example, the circular movement of the conveyer member in the pitching mechanism 6 may be provided by a different kind of driving mechanism such as a cam mechanism. Also, conveying of the test piece from the position correction mechanism to the photometric measurement mechanism many not necessarily be provided by a pitching movement; alternatively, a mechanism which moves the test piece in sliding movement may be employed. Still another example is the breaker mechanism 8 which includes the leaf spring member 80 rocked by the circular movement of the placement part 65 of the conveyer member 62 for breaking a pile of test pieces in the disposal box 12; the breaker mechanism may be anything else which exerts an amount of force necessary for breaking the pile of test pieces in the disposal box. Specifically, the breaker mechanism may be provided by e.g. a configuration which includes an element driven separately from the conveyer member for making interference with the pile of test pieces, a configuration for vibrating the disposal box, or a configuration for blowing air to the pile of test pieces.

The invention claimed is:

1. An analyzer for analyzing a sample, using an analysis piece provided with at least one reagent pad on a base material, the analyzer comprising:
    a placement part on which the analysis piece is placed; and
    a photometric measurer for photometric measurement of the analysis piece,
    the analysis piece being moved in a conveying direction from the placement part toward the photometric measurer,
    wherein the placement part is configured to hold the analysis piece in a first orientation in which a first end of the base material provided with said at least one reagent pad is oriented in a first direction perpendicular to the conveying direction with respect to a second end of the base material not provided with said at least one reagent pad, and a second orientation in which the first end is oriented in a second direction opposite to the first direction with respect to the second end, the second direction being perpendicular to the conveying direction and parallel to the first direction; and
    wherein the analyzer further comprises an orientation determiner for determining whether the analysis piece is in the first orientation or in the second orientation based on information from the photometric measurer.

2. The analyzer according to claim 1, wherein the analysis piece includes a first and a second reagent pads, and
    wherein the placement part is arranged to hold the analysis piece in the first orientation in which the first reagent pad is oriented in the first direction with respect to the second reagent pad, or the second orientation in which the first reagent pad is oriented in the second direction with respect to the second reagent pad.

3. The analyzer according to claim 2, wherein the analysis piece is conveyed from the placement part toward the photometric measurer, with the reagent pads lined in the first or second direction.

4. The analyzer according to claim 3, wherein the photometric measurer is farther from a front of the analyzer than the placement part, and
    wherein the analysis piece is conveyed from a side closer to the front toward a side farther from the front.

5. The analyzer according to claim 1, wherein the placement part is open in an upward direction as well as in the first and the second directions.

6. The analyzer according to claim 1, wherein the photometric measurer is capable of making a reciprocating travel between a first stand-by position provided on the side of the first direction and a second stand-by position provided on the side of the second direction, along the analysis piece, the analyzer further comprising:
    a controller for controlling an operation of the photometric measurer in such a way that the photometric measurer is moved from the first stand-by position to the second stand-by position and then made stand by at the second stand-by position if the photometric measurer is at the first stand-by position whereas the photometric measurer is moved from the second stand-by position to the first stand-by position and then made stand by at the first stand-by position if the photometric measurer is at the second stand-by position, for analysis of the analysis piece; and
    a computing part which makes calculation necessary for analyzing the sample for said at least one reagent pad, based on a result of photometric measurement at the photometric measurer during the travel of the photometric measurer from the first stand-by position to the second stand-by position or from the second stand-by position to the first stand-by position.

7. The analyzer according to claim 6, wherein the analysis piece includes a baseline part provided closely to said at least one reagent pad, and
    wherein the computing part makes calculation necessary for analyzing the sample by performing a first step of obtaining a time course of light reception amount during the travel of the photometric measurer from the first stand-by position to the second stand-by position or from the second stand-by position to the first stand-by position; a second step of detecting a baseline part data region representing the baseline part in the time course; and a third step of obtaining a reagent pad data region for each of the reagent pads, using the baseline part data region as a baseline.

8. The analyzer according to claim 7, wherein the computing part checks if the travel of the photometric measurer is from the first stand-by position to the second stand-by position or from the second stand-by position to the first stand-by position, and takes the travel direction of the photometric measurer into account when obtaining the reagent pad data regions in the third step.

9. The analyzer according to claim 7, wherein a dimension of said at least one reagent pad along the analysis piece is greater than a dimension of the baseline part along the analysis piece.

10. The analyzer according to claim 1, wherein a plurality of the analysis pieces are conveyed continually to the photometric measurer, the photometric measurer making photometric measurement successively with respect to the analysis pieces.

11. The analyzer according to claim 6, wherein the photometric measurer includes a plurality of light emitters and an optical receiver,
wherein the light emitters cast light diagonally to said at least one reagent pad, and
wherein the optical receiver receives reflected light coming upward from said at least one reagent pad.

12. The analyzer according to claim 11, wherein the light emitters are disposed in a point symmetry in plan view, with the optical receiver representing a center of the symmetry.

13. The analyzer according to claim 11, wherein the optical receiver is on a hypothetical straight line extending along the conveying direction, and
wherein the light emitters are disposed in a line symmetry in plan view, with respect to the hypothetical straight line.

14. The analyzer according to claim 1, further comprising a position corrector for correction of a positional variation of the analysis piece in the first and second directions, from a time of placement of the analysis piece onto the placement part to a time of photometric measurement at the photometric measurer.

15. The analyzer according to claim 14, wherein the position corrector selectively takes a state of restricting the analysis piece in the first and second directions, or a state of not restricting the analysis piece.

16. The analyzer according to claim 15, wherein the position corrector includes one or more pivoting members pivoted to select the state of restricting the analysis piece in the first and second directions or the state of not restricting the analysis piece.

17. The analyzer according to claim 16, wherein the pivoting members include a first and a second pivoting members each having a holding portion for restricting the analysis piece, the holding portions of the first and second pivoting members being able to toward and away from each other, and
wherein the position corrector restricts the analysis piece in the first and second directions by pivoting the first and second pivoting members to bring the holding portions toward each other, and ceases the restriction on the analysis piece in the first and second directions by pivoting the first and the second pivoting members to bring the holding portions away from each other.

18. The analyzer according to claim 17, further comprising a moving member capable of making a reciprocating movement in the conveying direction and in a retreating direction opposite thereto, for sliding the analysis piece toward a position provided with the first and second pivoting members,
wherein the first and second pivoting members pivot in association with the movement of the moving member.

19. The analyzer according to claim 18, wherein the first and second pivoting members pivot in a restricting direction to restrict the analysis piece in the first and second directions when the moving member changes its state from a non-interfering state to an interfering state, the first and second pivoting members also pivoting in a non-restricting direction not to restrict the analysis piece in the first and second directions when the mover changes its state from the interfering state to the non-interfering state.

20. The analyzer according to claim 19, wherein the first and second pivoting members have interference counter portions for interference with the moving member, the holding portions pivoting to restrict the analysis piece upon downward displacement of the interference counter portions,
wherein the moving member has an interferer for interference with the interference counter portions, and
wherein at least one of the interference counter portions and the interferer has a tapered surface for applying a downward force to the interference counter portions upon interference of the interferer with the interference counter portions.

21. The analyzer according to claim 20, wherein the interference counter portions protrude in a direction opposite to the conveying direction, and
wherein the interferer has the tapered surface and protrudes in the conveying direction.

22. The analyzer according to claim 14, wherein the position corrector corrects position variation of the analysis piece in the first and second directions while the analysis piece stops at a correction position provided between the placement part and the photometric measurer.

23. The analyzer according to claim 14, wherein correction of position variation of the analysis piece in the first and second directions is performed on a side closer to a front of the analyzer than a place provided with the position corrector.

24. The analyzer according to claim 23, wherein position variation of the analysis piece in the conveying direction is corrected by sandwiching the analysis piece between the moving member and an upright wall extending in the first and second directions.

25. The analyzer according to claim 24, further comprising an excess sample remover for removing excess sample from the analysis piece,
wherein the excess sample remover removes excess sample from the analysis piece while also correcting position variation of the analysis piece in the conveying direction by sandwiching the analysis piece between itself and the moving member.

26. The analyzer according to claim 25, wherein the excess sample remover removes excess sample by means of capillary force upon contact with the analysis piece.

27. The analyzer according to claim 25, wherein the analysis piece is moved over the excess sample remover to a position provided with the position corrector after contacting the excess sample remover.

28. The analyzer according to claim 1, further comprising:
a disposal box for storing analysis pieces which have undergone photometric measurement at the photometric measurer; and
a breaker mechanism for breaking a pile of analysis pieces in the disposal box.

29. The analyzer according to claim 28, wherein the breaker mechanism includes a contact element for making contact with the pile of analysis pieces in the disposal box.

30. The analyzer according to claim 29, wherein the breaker mechanism selectively takes a first state in which at least part of the contact element is in the disposal box for contact with the pile of analysis pieces and a second state in which the contact element is entirely out of the disposal box.

31. The analyzer according to claim 30, further comprising a conveying mechanism for conveying the analysis piece in the conveying direction for at least part of a conveying route of the analysis piece which extends from the placement part toward the photometric measurer,
wherein the conveying mechanism includes a rotating mover which rotates for conveying the analysis piece, and
wherein the contact element repeats a cycle of the first state and the second state in association with the movement of the rotating mover.

32. The analyzer according to claim 31, wherein the contact element is rocked by the rotating mover.

33. The analyzer according to claim 32, wherein the contact element is provided by a leaf spring.

34. An analyzer for analyzing a sample, using an analysis piece provided with a marker and at least one reagent pad on a base material, the analyzer comprising:
a placement part on which the analysis piece is placed;
a photometric measurer for photometric measurement of the marker and said at least one reagent pad of the analysis piece;
a computing part for analyzing information from the photometric measurer; and
a conveyor mechanism for moving the analysis piece in a conveying direction from the placement part toward the photometric measurer,
wherein the placement part is configured to hold the analysis piece in a first orientation in which a first end of the base material provided with said at least one reagent pad is oriented in a first direction perpendicular to the conveying direction with respect to a second end of the base material closer to the marker, and a second orientation in which the first end is oriented in a second direction opposite to the first direction with respect to the second end, the second direction being perpendicular to the conveying direction and parallel to the first direction; and
wherein the computing part comprises an orientation determiner that determines whether the analysis piece is in the first orientation or in the second orientation based on the information from the photometric measurer.

35. An analyzer for analyzing a sample, using an elongate analysis piece provided with at least one reagent pad on a base material, the base material including a first end provided with said at least one reagent pad, the base material also including a second end not provided with a reagent pad, the analyzer comprising:
a placement part on which the analysis piece is placed, the placement part being open sidewise at a first side and at a second side opposite to the first side lengthwise of the analysis piece that is placed on the placement part; and
a photometric measurer for photometric measurement of the analysis piece;
the analysis piece being moved in a conveying direction from the placement part toward the photometric measurer;
wherein the placement part is configured to hold the analysis piece in a first orientation in which the first end of the base material is located closer to the first side of the placement part than it is to the second side of the placement part, and a second orientation in which the first end is located closer to the second side of the placement part than it is to the first side of the placement part; and
wherein the analyzer further comprises an orientation determiner for determining whether the analysis piece is in the first orientation or in the second orientation based on information from the photometric measurer.

* * * * *

UNITED STATES PATENT AND TRADEMARK OFFICE
CERTIFICATE OF CORRECTION

| | | Page 1 of 1 |
|---|---|---|
| PATENT NO. | : 8,298,484 B2 | |
| APPLICATION NO. | : 11/579990 | |
| DATED | : October 30, 2012 | |
| INVENTOR(S) | : Takagi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 842 days.

Signed and Sealed this
Eleventh Day of November, 2014

Michelle K. Lee
*Deputy Director of the United States Patent and Trademark Office*